(12) United States Patent
Lockwood et al.

(10) Patent No.: US 8,246,592 B2
(45) Date of Patent: *Aug. 21, 2012

(54) VACUUM THERAPY AND CLEANSING DRESSING FOR WOUNDS

(75) Inventors: Jeffrey S. Lockwood, Batesville, IN (US); Robert Petrosenko, Batesville, IN (US); James Robert Risk, Jr., Milan, IN (US)

(73) Assignee: KCI Medical Resources, Grand Cayman (KY)

( * ) Notice: Subject to any disclaimer, the term of this patent is extended or adjusted under 35 U.S.C. 154(b) by 257 days.

This patent is subject to a terminal disclaimer.

(21) Appl. No.: 12/618,411

(22) Filed: Nov. 13, 2009

(65) Prior Publication Data

US 2010/0106117 A1 Apr. 29, 2010

Related U.S. Application Data

(60) Continuation of application No. 10/664,535, filed on Sep. 19, 2003, now Pat. No. 7,867,206, which is a division of application No. 09/725,352, filed on Nov. 29, 2000, now Pat. No. 6,685,681.

(51) Int. Cl.
*A61M 1/00* (2006.01)

(52) U.S. Cl. .......................... 604/313; 604/289; 604/304

(58) Field of Classification Search .......... 604/289–290, 604/304, 305, 310, 313, 315, 540, 541, 543, 604/317, 319, 321, 327, 355; 602/48; 601/6, 601/7, 9–11

See application file for complete search history.

(56) References Cited

U.S. PATENT DOCUMENTS

| | | | |
|---|---|---|---|
| 765,746 A | 7/1904 | Miner | 601/7 |
| 774,529 A | 11/1904 | Nieschang | 601/14 |
| 1,000,001 A | 8/1911 | Holz | 601/6 |
| 1,355,846 A | 10/1920 | Rannells | 604/286 |
| 1,385,346 A | 7/1921 | Taylor | 604/305 |
| 1,709,520 A | 4/1929 | Chandler | 292/259 R |
| 1,936,129 A | 11/1933 | Fisk | 604/313 |
| 2,078,180 A | 4/1937 | Kronenberg | 604/28 |
| 2,195,771 A | 4/1940 | Estler | 604/355 |
| 2,221,758 A | 11/1940 | Elmquist | 128/888 |
| 2,305,289 A | 12/1942 | Coburg | 128/132 |

(Continued)

FOREIGN PATENT DOCUMENTS

AU 550575 A1 8/1982

(Continued)

OTHER PUBLICATIONS

Notice of Allowance issued in U.S. Appl. No. 10/276,778, mailed Sep. 7, 2010.

(Continued)

*Primary Examiner* — Michele M Kidwell
(74) *Attorney, Agent, or Firm* — Fulbright & Jaworski

(57) ABSTRACT

Wound treatment apparatuses comprising a vacuum source and a bandage (e.g., a wound-care bandage) configured to be coupled (and/or coupled) to the vacuum source. Some embodiments of the bandage including a wound dressing member configured to be placed in contact with a wound surface, and a suction port associated with the wound dressing member and/or configured to be connected to the vacuum source. Some embodiments of the member including a plurality of spacers configured to contact the wound surface to define suction space between the member and the wound surface. Some embodiments of the member including holes configured to communicate with the suction space, and/or a plurality of passageways between the suction port and the holes.

24 Claims, 6 Drawing Sheets

U.S. PATENT DOCUMENTS

| | | | |
|---|---|---|---|
| 2,338,339 A | 1/1944 | LaMere et al. | 601/7 |
| 2,443,481 A | 6/1948 | Sene | 128/88 |
| 2,547,758 A | 4/1951 | Keeling | 128/349 |
| 2,560,915 A | 7/1951 | Bamberger | 128/350 |
| 2,573,791 A | 11/1951 | Howells | 602/14 |
| 2,577,945 A | 12/1951 | Altherton | 602/1 |
| 2,632,443 A | 3/1953 | Lesher | 128/888 |
| 2,682,873 A | 7/1954 | Evans et al. | 602/42 |
| 2,910,763 A | 11/1959 | Lauterbach | 128/72.2 |
| 2,969,057 A | 1/1961 | Simmons | 128/2 |
| 3,026,874 A | 3/1962 | Stevens | 604/305 |
| 3,066,672 A | 12/1962 | Crosby, Jr. et al. | 128/276 |
| 3,315,665 A | 4/1967 | MacLeod | 601/7 |
| 3,367,332 A | 2/1968 | Groves | 604/290 |
| 3,382,867 A | 5/1968 | Reaves | 601/7 |
| 3,430,631 A | 3/1969 | Abramson | 128/350 |
| 3,492,991 A | 2/1970 | Dryer | 604/6.09 |
| 3,520,300 A | 7/1970 | Flower et al. | 604/269 |
| 3,528,416 A | 9/1970 | Chamberlain | 128/888 |
| 3,568,675 A | 3/1971 | Harvey | 604/355 |
| 3,585,742 A | 6/1971 | Tyler | 40/642.02 |
| 3,599,639 A | 8/1971 | Spotz | 604/119 |
| 3,610,238 A | 10/1971 | Rich, Jr. | 604/23 |
| 3,623,087 A | 11/1971 | Gallichotte et al. | 340/509 |
| 3,626,087 A | 12/1971 | Tomioka | 178/5.4 |
| 3,648,692 A | 3/1972 | Wheeler | 602/46 |
| 3,682,180 A | 8/1972 | McFarlane | 128/350 |
| 3,683,894 A | 8/1972 | Villari | 600/580 |
| 3,721,244 A | 3/1973 | Elmaleh | 604/128 |
| 3,752,158 A | 8/1973 | Kariher | 604/133 |
| 3,753,439 A | 8/1973 | Brugarolas et al. | 128/350 |
| 3,782,377 A | 1/1974 | Rychlik | 128/888 |
| 3,812,972 A | 5/1974 | Rosenblum | 210/489 |
| 3,814,095 A | 6/1974 | Lubens | 604/307 |
| 3,817,145 A | 6/1974 | Cohen | 84/471 |
| 3,823,720 A | 7/1974 | Tribble | 128/350 |
| 3,826,254 A | 7/1974 | Mellor | 128/133 |
| 3,831,588 A | 8/1974 | Rindner | 600/488 |
| 3,860,008 A | 1/1975 | Miner et al. | 128/350 |
| 3,874,387 A | 4/1975 | Barbieri | 602/53 |
| 3,903,882 A | 9/1975 | Augurt | 602/43 |
| 3,924,624 A | 12/1975 | Schachet | 128/276 |
| 3,935,863 A | 2/1976 | Kliger | 604/369 |
| 3,954,105 A | 5/1976 | Nordby et al. | 604/355 |
| 3,982,546 A | 9/1976 | Friend | 604/249 |
| 4,004,590 A | 1/1977 | Muriot | 604/326 |
| 4,013,076 A | 3/1977 | Puderbaugh et al. | 604/320 |
| RE29,319 E | 7/1977 | Nordby et al. | 604/355 |
| RE29,321 E | 7/1977 | Holbrook | 215/309 |
| 4,058,123 A | 11/1977 | May | 128/278 |
| 4,080,970 A | 3/1978 | Miller | 604/174 |
| 4,096,853 A | 6/1978 | Weigand | 128/2 |
| 4,112,947 A | 9/1978 | Nehring | 604/30 |
| 4,139,004 A | 2/1979 | Gonzalez, Jr. | 602/14 |
| 4,149,541 A | 4/1979 | Gammons et al. | 607/104 |
| 4,165,748 A | 8/1979 | Johnson | 128/348 |
| 4,178,974 A | 12/1979 | Levin | 141/51 |
| 4,184,510 A | 1/1980 | Murry et al. | 137/565 |
| 4,191,204 A | 3/1980 | Nehring | 137/205 |
| 4,219,021 A | 8/1980 | Fink | 128/214 |
| 4,224,941 A | 9/1980 | Stivala | 604/23 |
| 4,233,969 A | 11/1980 | Lock et al. | 128/156 |
| 4,245,630 A | 1/1981 | Lloyd et al. | 128/155 |
| 4,250,882 A | 2/1981 | Adair | 604/355 |
| 4,256,109 A | 3/1981 | Nichols | 128/276 |
| 4,261,363 A | 4/1981 | Russo | 128/350 |
| 4,275,721 A | 6/1981 | Olson | 604/180 |
| 4,284,079 A | 8/1981 | Adair | 128/295 |
| 4,297,995 A | 11/1981 | Golub | 604/304 |
| 4,333,468 A | 6/1982 | Geist | 128/348 |
| 4,341,209 A | 7/1982 | Schaar | 602/58 |
| 4,364,394 A | 12/1982 | Wilkinson | 604/96 |
| 4,373,519 A | 2/1983 | Errede et al. | 602/43 |
| 4,382,441 A | 5/1983 | Svedman | 604/291 |
| 4,392,853 A | 7/1983 | Muto | 604/171 |
| 4,392,858 A | 7/1983 | George et al. | 604/187 |
| 4,399,816 A | 8/1983 | Spangler | 128/888 |
| 4,419,097 A | 12/1983 | Rowland | 604/174 |
| 4,445,897 A | 5/1984 | Ekbladh et al. | 604/280 |
| 4,457,755 A | 7/1984 | Wilson | 604/184 |
| 4,460,370 A | 7/1984 | Allison et al. | 424/448 |
| 4,465,062 A | 8/1984 | Versaggi et al. | 128/897 |
| 4,465,485 A | 8/1984 | Kashmer et al. | 604/320 |
| 4,469,092 A | 9/1984 | Marshall et al. | 601/70 |
| 4,475,909 A | 10/1984 | Eisenberg | 604/349 |
| 4,480,638 A | 11/1984 | Schmid | 128/155 |
| 4,508,533 A | 4/1985 | Abramson | 604/35 |
| 4,525,156 A | 6/1985 | Benusa et al. | 604/28 |
| 4,525,166 A | 6/1985 | Leclerc | 604/133 |
| 4,525,374 A | 6/1985 | Vaillancourt | 427/2 |
| 4,533,352 A | 8/1985 | Van Beek et al. | 604/317 |
| 4,533,419 A | 8/1985 | Pieslak et al. | 156/85 |
| 4,540,412 A | 9/1985 | Van Overloop | 604/291 |
| 4,543,100 A | 9/1985 | Brodsky | 604/180 |
| 4,548,202 A | 10/1985 | Duncan | 128/334 |
| 4,551,139 A | 11/1985 | Plaas et al. | 604/290 |
| 4,553,967 A | 11/1985 | Ferguson et al. | 604/317 |
| 4,569,348 A | 2/1986 | Hasslinger | 604/179 |
| 4,569,674 A | 2/1986 | Phillips et al. | 604/119 |
| 4,573,965 A | 3/1986 | Russo | 604/30 |
| 4,579,555 A | 4/1986 | Russo | 604/541 |
| 4,596,564 A | 6/1986 | Spetzler et al. | 604/281 |
| 4,605,399 A | 8/1986 | Weston et al. | 604/305 |
| 4,608,041 A | 8/1986 | Nielsen | 604/23 |
| 4,614,794 A | 9/1986 | Easton et al. | 530/356 |
| 4,624,656 A | 11/1986 | Clark et al. | 604/23 |
| 4,633,863 A | 1/1987 | Filips et al. | 128/846 |
| 4,637,819 A | 1/1987 | Ouellette et al. | 604/369 |
| 4,640,688 A | 2/1987 | Hauser | 604/352 |
| 4,641,643 A | 2/1987 | Greer | 128/888 |
| 4,645,492 A | 2/1987 | Weeks | 604/174 |
| 4,655,210 A | 4/1987 | Edenbaum et al. | 602/46 |
| 4,655,754 A | 4/1987 | Richmond et al. | 604/323 |
| 4,661,093 A | 4/1987 | Beck et al. | 604/543 |
| 4,664,652 A | 5/1987 | Weilbacher | 604/133 |
| 4,664,662 A | 5/1987 | Webster | 602/47 |
| 4,667,666 A | 5/1987 | Frysliie | 128/888 |
| 4,679,590 A | 7/1987 | Hergenroeer | 137/602 |
| 4,704,102 A | 11/1987 | Guthery | 604/28 |
| 4,710,165 A | 12/1987 | McNeil et al. | 604/67 |
| 4,713,051 A | 12/1987 | Steppe et al. | 604/30 |
| 4,717,332 A | 1/1988 | Edens | 431/8 |
| 4,717,379 A | 1/1988 | Ekholmer | 604/43 |
| 4,717,382 A | 1/1988 | Clemens et al. | 604/122 |
| 4,728,323 A | 3/1988 | Matson | 604/304 |
| 4,733,659 A | 3/1988 | Edenbaum et al. | 602/54 |
| 4,735,606 A | 4/1988 | Davison | 604/28 |
| 4,735,610 A | 4/1988 | Akkas et al. | 604/119 |
| 4,737,148 A | 4/1988 | Blake | 604/126 |
| 4,740,202 A | 4/1988 | Stacey et al. | 604/119 |
| 4,743,232 A | 5/1988 | Kruger | 604/180 |
| 4,747,166 A | 5/1988 | Kuntz | 4/144.1 |
| 4,758,220 A | 7/1988 | Sundblom et al. | 604/65 |
| 4,759,354 A | 7/1988 | Quarfoot | 602/50 |
| 4,765,316 A | 8/1988 | Marshall | 601/70 |
| 4,778,446 A | 10/1988 | Jensen | 604/27 |
| 4,778,456 A | 10/1988 | Lokken | 604/290 |
| 4,787,888 A | 11/1988 | Fox | 604/20 |
| 4,795,428 A | 1/1989 | Hwang | 604/73 |
| 4,798,578 A | 1/1989 | Ranford | 604/6.09 |
| 4,820,265 A | 4/1989 | DeSatnick et al. | 604/30 |
| 4,820,284 A | 4/1989 | Hauri | 604/318 |
| 4,826,494 A | 5/1989 | Richmond et al. | 604/323 |
| 4,826,949 A | 5/1989 | Stanko | 528/272 |
| 4,834,110 A | 5/1989 | Richard | 600/573 |
| 4,838,883 A | 6/1989 | Matsuura | 604/349 |
| 4,840,187 A | 6/1989 | Brazier | 128/844 |
| 4,841,962 A | 6/1989 | Berg et al. | 128/156 |
| 4,850,350 A | 7/1989 | Jackson | 128/207.16 |
| 4,863,449 A | 9/1989 | Therriault et al. | 604/352 |
| 4,872,450 A | 10/1989 | Austard | 602/48 |
| 4,878,901 A | 11/1989 | Sachse | 604/174 |
| 4,890,608 A | 1/1990 | Steer | 602/57 |
| 4,897,081 A | 1/1990 | Poirer et al. | 604/175 |
| 4,900,302 A | 2/1990 | Newton | 604/30 |
| 4,902,508 A | 2/1990 | Badylak et al. | 424/95 |
| 4,906,233 A | 3/1990 | Moriuchi et al. | 604/174 |

| Patent | Date | Inventor | Class |
|---|---|---|---|
| 4,906,240 A | 3/1990 | Reed et al. | 604/307 |
| 4,915,694 A | 4/1990 | Yamamoto et al. | 604/180 |
| 4,917,112 A | 4/1990 | Kalt | 602/58 |
| 4,919,654 A | 4/1990 | Kalt | 604/180 |
| 4,921,492 A | 5/1990 | Schultz et al. | 604/315 |
| 4,930,997 A | 6/1990 | Bennett | 471/410 |
| 4,941,882 A | 7/1990 | Ward et al. | 604/180 |
| 4,950,230 A | 8/1990 | Kendell | 604/28 |
| 4,953,565 A | 9/1990 | Tachibana et al. | 607/152 |
| 4,956,178 A | 9/1990 | Badylak et al. | 424/551 |
| 4,957,492 A | 9/1990 | McVay | 604/319 |
| 4,962,761 A | 10/1990 | Golden | 607/104 |
| 4,969,880 A | 11/1990 | Zamierowski | 604/305 |
| 4,969,881 A | 11/1990 | Viesturs | 604/305 |
| 4,970,298 A | 11/1990 | Silver et al. | 530/356 |
| 4,985,019 A | 1/1991 | Michelson | 604/140 |
| 4,988,336 A | 1/1991 | Kohn | 604/67 |
| 4,990,144 A | 2/1991 | Blott | 604/304 |
| 4,991,574 A | 2/1991 | Pocknell | 602/48 |
| 4,994,022 A | 2/1991 | Steffler et al. | 604/7 |
| 4,997,425 A | 3/1991 | Shioya et al. | 604/304 |
| 5,000,172 A | 3/1991 | Ward | 128/155 |
| 5,000,741 A | 3/1991 | Kalt | 604/180 |
| 5,002,528 A | 3/1991 | Palestrant | 604/28 |
| 5,002,529 A | 3/1991 | Cunningham | 604/73 |
| 5,003,971 A | 4/1991 | Buckley | 602/54 |
| 5,014,389 A | 5/1991 | Ogilvie et al. | 15/353 |
| 5,034,003 A | 7/1991 | Denance | 604/117 |
| 5,034,006 A | 7/1991 | Hosoda et al. | 604/317 |
| 5,035,865 A | 7/1991 | Inaba et al. | 422/99 |
| 5,037,397 A | 8/1991 | Kalt et al. | 604/174 |
| 5,042,978 A | 8/1991 | Quenin et al. | 604/317 |
| 5,045,777 A | 9/1991 | Itagaki | 324/76.12 |
| 5,060,662 A | 10/1991 | Farnsworth, III | 128/888 |
| 5,069,907 A | 12/1991 | Mixon et al. | 424/445 |
| 5,071,409 A | 12/1991 | Rosenberg | 604/119 |
| 5,073,172 A | 12/1991 | Fell | 604/319 |
| 5,080,650 A | 1/1992 | Hirsch et al. | 604/104 |
| 5,086,170 A | 2/1992 | Luheshi et al. | 540/103 |
| 5,086,763 A | 2/1992 | Hathman | 602/42 |
| 5,086,764 A | 2/1992 | Gilman | 602/42 |
| 5,092,858 A | 3/1992 | Benson et al. | 604/319 |
| 5,100,395 A | 3/1992 | Rosenberg | 604/284 |
| 5,100,396 A | 3/1992 | Zamierowski | 604/305 |
| 5,101,808 A | 4/1992 | Kobayashi et al. | 601/44 |
| 5,106,362 A | 4/1992 | Gilman | 602/47 |
| 5,106,629 A | 4/1992 | Cartmell et al. | 424/445 |
| 5,108,364 A | 4/1992 | Takezawa et al. | 604/43 |
| 5,134,994 A | 8/1992 | Say | 128/200.24 |
| 5,135,518 A | 8/1992 | Vera | 604/291 |
| 5,146,925 A | 9/1992 | Snow | 600/435 |
| 5,147,338 A | 9/1992 | Lang et al. | 604/304 |
| 5,149,331 A | 9/1992 | Ferdman et al. | 604/290 |
| 5,152,757 A | 10/1992 | Erikson | 604/305 |
| 5,160,322 A | 11/1992 | Scheremet et al. | 604/122 |
| 5,167,613 A | 12/1992 | Karami et al. | 602/42 |
| 5,167,622 A | 12/1992 | Muto | 604/35 |
| 5,170,781 A | 12/1992 | Loomis | 128/118.1 |
| 5,176,502 A | 1/1993 | Sanderson et al. | 417/18 |
| 5,176,663 A | 1/1993 | Svedman et al. | 604/305 |
| 5,176,667 A | 1/1993 | DeBring | 604/356 |
| 5,181,908 A | 1/1993 | Bell | 604/24 |
| 5,189,609 A | 2/1993 | Tivig et al. | 600/300 |
| 5,197,948 A | 3/1993 | Ghodsian | 604/30 |
| 5,215,522 A | 6/1993 | Page et al. | 604/33 |
| 5,215,539 A | 6/1993 | Schoolman | 604/541 |
| 5,224,929 A | 7/1993 | Remiszewski | 604/30 |
| 5,228,431 A | 7/1993 | Giarretto | 601/9 |
| 5,230,350 A | 7/1993 | Fentress | 128/846 |
| 5,232,453 A | 8/1993 | Plass et al. | 604/180 |
| 5,238,654 A | 8/1993 | Nohl et al. | 422/100 |
| 5,249,121 A | 9/1993 | Baum et al. | 606/1 |
| 5,256,418 A | 10/1993 | Kemp et al. | 424/423 |
| 5,261,893 A | 11/1993 | Zamierowski | 604/180 |
| 5,263,922 A | 11/1993 | Sova et al. | 602/59 |
| 5,265,605 A | 11/1993 | Afflerbach | 600/300 |
| 5,275,826 A | 1/1994 | Badylak et al. | 424/551 |
| 5,278,100 A | 1/1994 | Doan et al. | 437/200 |
| 5,279,550 A | 1/1994 | Habib et al. | 604/38 |
| 5,281,422 A | 1/1994 | Badylak et al. | 424/551 |
| 5,291,887 A | 3/1994 | Stanley et al. | 600/529 |
| 5,298,015 A | 3/1994 | Komatsuzaki et al. | 602/46 |
| 5,306,298 A | 4/1994 | Godley, III et al. | 623/9 |
| 5,314,409 A | 5/1994 | Sarosiek et al. | 604/101 |
| 5,330,452 A | 7/1994 | Zook | 604/307 |
| 5,335,651 A | 8/1994 | Foster et al. | 128/202.13 |
| 5,338,293 A | 8/1994 | Jeppsson et al. | 604/29 |
| 5,342,293 A | 8/1994 | Zanger | 604/22 |
| 5,342,301 A | 8/1994 | Saab | 604/96 |
| 5,342,376 A | 8/1994 | Ruff | 606/151 |
| 5,344,415 A | 9/1994 | DeBusk et al. | 604/304 |
| 5,349,965 A | 9/1994 | McCarver | 128/846 |
| 5,352,463 A | 10/1994 | Badylak et al. | 424/551 |
| 5,358,494 A | 10/1994 | Svedman | 604/313 |
| 5,370,610 A | 12/1994 | Reynolds | 604/43 |
| 5,372,821 A | 12/1994 | Badylak et al. | 424/551 |
| 5,374,254 A | 12/1994 | Burma | 604/175 |
| 5,376,252 A | 12/1994 | Ekstrom et al. | 204/603 |
| 5,380,280 A | 1/1995 | Peterson | 604/65 |
| 5,395,315 A | 3/1995 | Griep | 604/35 |
| 5,409,013 A | 4/1995 | Clement | 128/753 |
| 5,413,788 A | 5/1995 | Edwards et al. | 424/409 |
| 5,419,768 A | 5/1995 | Kayser | 604/119 |
| 5,431,622 A | 7/1995 | Pyrozyk et al. | 602/2 |
| 5,437,622 A | 8/1995 | Carion | 602/57 |
| 5,437,651 A | 8/1995 | Todd et al. | 604/313 |
| 5,439,452 A | 8/1995 | McCarty | 604/248 |
| 5,445,604 A | 8/1995 | Lang | 602/47 |
| 5,445,833 A | 8/1995 | Badylak et al. | 424/551 |
| 5,447,505 A | 9/1995 | Valentine et al. | 604/304 |
| 5,449,383 A | 9/1995 | Chatelier et al. | 623/1 |
| 5,451,215 A | 9/1995 | Wolter | 604/265 |
| 5,451,373 A | 9/1995 | Lewis et al. | 422/82.13 |
| 5,478,333 A | 12/1995 | Asherman, Jr. | 604/304 |
| 5,484,420 A | 1/1996 | Russo | 604/178 |
| 5,484,427 A | 1/1996 | Gibbons | 604/313 |
| 5,484,428 A | 1/1996 | Drainville et al. | 604/319 |
| 5,487,889 A | 1/1996 | Eckert et al. | 424/93.1 |
| 5,516,533 A | 5/1996 | Badylak et al. | 424/551 |
| 5,520,652 A | 5/1996 | Peterson | 604/119 |
| 5,527,293 A | 6/1996 | Zamierowski | 604/176 |
| 5,531,670 A | 7/1996 | Westby et al. | 602/41 |
| 5,533,981 A | 7/1996 | Mandro et al. | 604/208 |
| 5,534,346 A | 7/1996 | Robinson | 428/343 |
| 5,540,668 A | 7/1996 | Wilson et al. | 604/248 |
| 5,542,918 A | 8/1996 | Atkinson | 604/27 |
| 5,549,584 A | 8/1996 | Gross | 604/313 |
| 5,554,389 A | 9/1996 | Badylak et al. | 424/558 |
| 5,556,375 A | 9/1996 | Ewall | 602/58 |
| 5,558,639 A | 9/1996 | Gangemi et al. | 604/67 |
| 5,573,784 A | 11/1996 | Badylak et al. | 424/551 |
| 5,578,022 A | 11/1996 | Scherson et al. | 604/304 |
| 5,578,662 A | 11/1996 | Bennett et al. | 524/54 |
| 5,607,388 A | 3/1997 | Ewall | 602/58 |
| 5,607,683 A | 3/1997 | Capelli | 424/405 |
| 5,616,338 A | 4/1997 | Fox et al. | 424/423 |
| 5,621,035 A | 4/1997 | Lyles et al. | 524/404 |
| 5,624,417 A | 4/1997 | Cook | 604/319 |
| 5,624,418 A | 4/1997 | Shepard | 604/319 |
| 5,628,735 A | 5/1997 | Skow | 604/317 |
| 5,629,186 A | 5/1997 | Yasukawa et al. | 435/177 |
| 5,631,011 A | 5/1997 | Wadström | 424/400 |
| 5,635,201 A | 6/1997 | Fabo | 424/443 |
| 5,636,643 A | 6/1997 | Argenta et al. | 128/897 |
| 5,641,518 A | 6/1997 | Badylak et al. | 424/551 |
| 5,645,081 A | 7/1997 | Argenta et al. | 128/897 |
| 5,645,860 A | 7/1997 | Knapp et al. | 424/551 |
| 5,655,258 A | 8/1997 | Heintz | 15/415.1 |
| 5,656,027 A | 8/1997 | Ellingboe | 604/541 |
| 5,662,598 A | 9/1997 | Tobin | 602/41 |
| 5,662,624 A | 9/1997 | Sundstrom et al. | 604/291 |
| 5,662,625 A | 9/1997 | Westwood | 604/305 |
| 5,669,892 A | 9/1997 | Keogh et al. | 604/320 |
| 5,672,151 A | 9/1997 | Calderon-Garciduñas | 602/21 |
| 5,672,152 A | 9/1997 | Mason et al. | 602/26 |
| 5,674,193 A | 10/1997 | Hayes | 604/28 |
| 5,678,564 A | 10/1997 | Lawrence et al. | 600/574 |
| 5,681,290 A | 10/1997 | Alexander | 604/180 |

| Patent | Kind | Date | Inventor | Class |
|---|---|---|---|---|
| 5,690,815 | A | 11/1997 | Krasnoff et al. | 210/97 |
| 5,695,998 | A | 12/1997 | Badylak et al. | 435/391 |
| 5,697,920 | A | 12/1997 | Gibbons | 604/289 |
| 5,711,969 | A | 1/1998 | Patel et al. | 424/551 |
| 5,718,955 | A | 2/1998 | McGuire et al. | 428/35.7 |
| 5,735,833 | A | 4/1998 | Olson | 604/289 |
| 5,738,656 | A | 4/1998 | Wagner | 604/119 |
| 5,741,237 | A | 4/1998 | Walker | 604/317 |
| 5,749,842 | A | 5/1998 | Cheong et al. | 602/41 |
| 5,753,267 | A | 5/1998 | Badylak et al. | 424/551 |
| 5,755,791 | A | 5/1998 | Whitson et al. | 623/15 |
| 5,759,570 | A | 6/1998 | Arnold | 424/443 |
| 5,762,640 | A | 6/1998 | Kajiwara et al. | 604/313 |
| 5,762,966 | A | 6/1998 | Knapp et al. | 424/551 |
| 5,780,281 | A | 7/1998 | Yasukawa et al. | 435/176 |
| 5,782,871 | A | 7/1998 | Fujiwara et al. | 604/313 |
| 5,795,584 | A | 8/1998 | Totakura et al. | 424/426 |
| 5,800,383 | A | 9/1998 | Chandler et al. | 604/35 |
| 5,817,145 | A | 10/1998 | Augustine et al. | 607/96 |
| 5,827,246 | A | 10/1998 | Bowen | 604/313 |
| 5,827,296 | A | 10/1998 | Morris et al. | 606/129 |
| 5,855,619 | A | 1/1999 | Caplan et al. | 623/11 |
| 5,866,414 | A | 2/1999 | Badylak et al. | 435/325 |
| 5,881,723 | A | 3/1999 | Wallace et al. | 128/204.21 |
| 5,891,111 | A | 4/1999 | Ismael | 604/280 |
| 5,902,874 | A | 5/1999 | Roby et al. | 528/310 |
| 5,902,875 | A | 5/1999 | Roby et al. | 528/310 |
| 5,911,222 | A | 6/1999 | Lawrence et al. | 600/574 |
| 5,914,387 | A | 6/1999 | Roby et al. | 528/310 |
| 5,919,476 | A | 7/1999 | Fischer et al. | 424/443 |
| 5,921,972 | A | 7/1999 | Skow | 604/313 |
| 5,928,174 | A | 7/1999 | Gibbins | 602/41 |
| 5,931,304 | A | 8/1999 | Hammond | 206/570 |
| 5,941,859 | A | 8/1999 | Lerman | 604/289 |
| 5,942,496 | A | 8/1999 | Bonadio et al. | 514/44 |
| 5,947,914 | A | 9/1999 | Augustine | 602/2 |
| 5,951,295 | A | 9/1999 | Lyles et al. | 433/228.1 |
| 5,954,680 | A | 9/1999 | Augustine | 602/42 |
| 5,961,480 | A | 10/1999 | Augustine | 602/41 |
| 5,962,427 | A | 10/1999 | Goldstein et al. | 514/44 |
| 5,964,721 | A | 10/1999 | Augustine | 602/2 |
| 5,964,723 | A | 10/1999 | Augustine | 602/42 |
| 5,986,163 | A | 11/1999 | Augustine | 602/42 |
| 5,997,568 | A | 12/1999 | Liu | 606/228 |
| 6,010,527 | A | 1/2000 | Augustine et al. | 607/96 |
| 6,013,048 | A | 1/2000 | Podany et al. | 604/22 |
| 6,017,493 | A | 1/2000 | Cambron et al. | 422/44 |
| 6,039,724 | A | 3/2000 | Seifert et al. | 604/533 |
| 6,040,493 | A * | 3/2000 | Cooke et al. | 602/41 |
| 6,045,518 | A | 4/2000 | Augustine | 602/2 |
| 6,045,541 | A | 4/2000 | Matsumoto et al. | 604/313 |
| 6,051,747 | A | 4/2000 | Lindqvist et al. | 602/46 |
| 6,056,730 | A | 5/2000 | Greter | 604/319 |
| 6,071,254 | A | 6/2000 | Augustine | 602/2 |
| 6,071,267 | A | 6/2000 | Zamierowski | 604/289 |
| 6,071,304 | A | 6/2000 | Augustine et al. | 607/96 |
| 6,080,189 | A | 6/2000 | Augustine et al. | 607/96 |
| 6,080,243 | A | 6/2000 | Insley et al. | 134/21 |
| 6,093,160 | A | 7/2000 | Augustine et al. | 602/2 |
| 6,093,230 | A | 7/2000 | Johnson et al. | 55/482 |
| 6,095,992 | A | 8/2000 | Augustine et al. | 602/2 |
| 6,099,567 | A | 8/2000 | Badylak et al. | 623/13 |
| 6,110,197 | A | 8/2000 | Augustine | 607/108 |
| 6,113,561 | A | 9/2000 | Augustine | 602/2 |
| 6,117,111 | A | 9/2000 | Fleischmann | 604/180 |
| 6,135,116 | A | 10/2000 | Vogel et al. | 128/898 |
| 6,142,982 | A | 11/2000 | Hunt et al. | 604/313 |
| 6,143,945 | A | 11/2000 | Augustine et al. | 602/41 |
| 6,149,614 | A | 11/2000 | Dunshee et al. | 602/57 |
| 6,171,344 | B1 | 1/2001 | Atala | 623/23.64 |
| 6,174,306 | B1 | 1/2001 | Fleischmann | 604/543 |
| 6,203,563 | B1 | 3/2001 | Fernandez | 606/215 |
| 6,206,931 | B1 | 3/2001 | Cook et al. | 623/23.75 |
| 6,207,875 | B1 | 3/2001 | Lindqvist et al. | 602/46 |
| 6,213,965 | B1 | 4/2001 | Augustine et al. | 602/2 |
| 6,213,966 | B1 | 4/2001 | Augustine | 602/2 |
| 6,217,535 | B1 | 4/2001 | Augustine | 602/2 |
| 6,235,009 | B1 | 5/2001 | Skow | 604/317 |
| 6,235,047 | B1 | 5/2001 | Augustine et al. | 607/96 |
| 6,241,697 | B1 | 6/2001 | Augustine | 602/2 |
| 6,241,698 | B1 | 6/2001 | Augustine | 602/2 |
| 6,241,747 | B1 | 6/2001 | Ruff | 606/216 |
| 6,244,311 | B1 | 6/2001 | Hand et al. | 141/375 |
| 6,248,084 | B1 | 6/2001 | Augustine et al. | 602/2 |
| 6,254,557 | B1 | 7/2001 | Augustine et al. | 602/2 |
| 6,254,580 | B1 | 7/2001 | Svedman | 604/313 |
| 6,259,067 | B1 | 7/2001 | Faries, Jr. et al. | 219/428 |
| 6,264,622 | B1 | 7/2001 | Augustine | 602/2 |
| 6,264,979 | B1 | 7/2001 | Svedman | 424/449 |
| 6,267,740 | B1 | 7/2001 | Augustine | 602/2 |
| 6,283,931 | B1 | 9/2001 | Augustine | 602/2 |
| 6,284,941 | B1 | 9/2001 | Cox et al. | 602/48 |
| 6,287,316 | B1 | 9/2001 | Agarwal et al. | 606/151 |
| 6,290,685 | B1 | 9/2001 | Insley et al. | 604/317 |
| 6,293,917 | B1 | 9/2001 | Augustine et al. | 602/2 |
| 6,325,798 | B1 | 12/2001 | Edwards et al. | 606/41 |
| 6,345,623 | B1 | 2/2002 | Heaton et al. | 128/897 |
| 6,364,853 | B1 | 4/2002 | French et al. | 604/35 |
| 6,394,142 | B1 | 5/2002 | Woelfel et al. | 138/115 |
| 6,398,767 | B1 | 6/2002 | Fleischmann | 604/313 |
| 6,410,427 | B1 | 6/2002 | Hu | 438/655 |
| 6,440,427 | B1 | 8/2002 | Wadström | 424/400 |
| 6,458,109 | B1 | 10/2002 | Henley et al. | 604/304 |
| 6,471,685 | B1 | 10/2002 | Johnson | 604/890.1 |
| 6,472,581 | B1 | 10/2002 | Muramatsu et al. | 602/41 |
| 6,488,643 | B1 | 12/2002 | Turney et al. | 602/13 |
| 6,491,682 | B2 | 12/2002 | Paderni | 604/541 |
| 6,491,693 | B1 | 12/2002 | Lytinaas | 606/53 |
| 6,493,568 | B1 | 12/2002 | Bell et al. | 600/323 |
| 6,500,112 | B1 | 12/2002 | Khouri | 600/38 |
| 6,520,982 | B1 | 2/2003 | Boynton et al. | 607/104 |
| 6,553,998 | B2 | 4/2003 | Heaton et al. | 128/897 |
| 6,557,704 | B1 | 5/2003 | Randolph | 206/363 |
| 6,559,773 | B1 | 5/2003 | Berry | 340/815.4 |
| 6,599,277 | B2 | 7/2003 | Neubert | 604/317 |
| 6,626,891 | B2 | 9/2003 | Ohmstede | 604/543 |
| 6,638,270 | B2 | 10/2003 | Johnson | 604/890.1 |
| 6,648,862 | B2 | 11/2003 | Watson | 604/319 |
| 6,663,349 | B1 | 12/2003 | Disenzo et al. | 417/44.1 |
| 6,685,681 | B2 | 2/2004 | Lockwood et al. | 604/305 |
| 6,691,047 | B1 | 2/2004 | Friedericks | 702/47 |
| 6,695,823 | B1 | 2/2004 | Lina et al. | 604/304 |
| 6,695,824 | B2 | 2/2004 | Howard et al. | 604/305 |
| 6,719,779 | B2 | 4/2004 | Daoud | 607/105 |
| 6,749,592 | B2 | 6/2004 | Lord | 604/319 |
| 6,752,794 | B2 | 6/2004 | Lockwood et al. | 604/313 |
| 6,755,807 | B2 | 6/2004 | Risk, Jr. et al. | 604/319 |
| 6,764,462 | B2 | 7/2004 | Risk, Jr. et al. | 604/67 |
| 6,767,334 | B1 | 7/2004 | Randolph | 604/35 |
| 6,794,554 | B2 | 9/2004 | Sessions et al. | 602/46 |
| 6,800,074 | B2 | 10/2004 | Henley et al. | 604/319 |
| 6,814,079 | B2 | 11/2004 | Heaton et al. | 128/897 |
| 6,824,533 | B2 | 11/2004 | Risk, Jr. et al. | 604/319 |
| 6,855,135 | B2 | 2/2005 | Lockwood et al. | 604/313 |
| 6,856,821 | B2 | 2/2005 | Johnson | 600/345 |
| 6,936,037 | B2 | 8/2005 | Bubb et al. | 604/327 |
| 6,951,553 | B2 | 10/2005 | Bubb et al. | 604/327 |
| 6,966,889 | B2 | 11/2005 | Saab | 604/96.01 |
| 6,979,324 | B2 | 12/2005 | Bybordi et al. | 604/313 |
| 6,994,702 | B1 | 2/2006 | Johnson | 606/9 |
| 6,994,708 | B2 | 2/2006 | Manzo | 606/45 |
| 7,004,915 | B2 | 2/2006 | Boynton et al. | 601/6 |
| 7,022,113 | B2 | 4/2006 | Lockwood et al. | 604/313 |
| 7,070,584 | B2 | 7/2006 | Johnson et al. | 604/313 |
| 7,077,832 | B2 | 7/2006 | Fleischmann | 604/304 |
| 7,108,683 | B2 | 9/2006 | Zamierowski | 604/313 |
| 7,117,869 | B2 | 10/2006 | Heaton et al. | 128/897 |
| 7,128,735 | B2 | 10/2006 | Weston | 604/543 |
| 7,144,390 | B1 | 12/2006 | Hannigan et al. | 604/313 |
| 7,195,624 | B2 | 3/2007 | Lockwood et al. | 604/543 |
| 7,216,651 | B2 | 5/2007 | Argenta et al. | 128/897 |
| 7,245,291 | B2 | 7/2007 | Sharif et al. | 345/172 |
| 7,273,054 | B2 | 9/2007 | Heaton et al. | 128/897 |
| 7,276,051 | B1 | 10/2007 | Henley et al. | 604/304 |
| 7,338,482 | B2 | 3/2008 | Lockwood et al. | 604/543 |
| 7,351,250 | B2 | 4/2008 | Zamierowski | 606/215 |
| 7,381,211 | B2 | 6/2008 | Zamierowski | 606/215 |
| 7,381,859 | B2 | 6/2008 | Hunt | 602/46 |

| Patent No. | Date | Inventor | Class |
|---|---|---|---|
| 7,410,495 B2 | 8/2008 | Zamierowski | 606/216 |
| 7,413,570 B2 | 8/2008 | Zamierowski | 606/215 |
| 7,413,571 B2 | 8/2008 | Zamierowski | 606/215 |
| 7,422,576 B2 | 9/2008 | Boynton et al. | 607/104 |
| 7,524,286 B2 | 4/2009 | Johnson | 600/309 |
| 7,534,927 B2 | 5/2009 | Lockwood et al. | 602/46 |
| 7,618,382 B2 | 11/2009 | Vogel et al. | 601/7 |
| 2001/0029956 A1 | 10/2001 | Argenta et al. | 128/897 |
| 2001/0043943 A1 | 11/2001 | Coffey | 424/447 |
| 2001/0052681 A1 | 12/2001 | Deavila | 280/47.19 |
| 2002/0077661 A1 | 6/2002 | Saadat | 606/221 |
| 2002/0082567 A1 | 6/2002 | Lockwood et al. | 604/313 |
| 2002/0082688 A1 | 6/2002 | Sander et al. | 623/2.13 |
| 2002/0085952 A1 | 7/2002 | Ellingboe et al. | 422/45 |
| 2002/0115951 A1 | 8/2002 | Norstrem et al. | 602/27 |
| 2002/0115952 A1 | 8/2002 | Johnson et al. | 602/41 |
| 2002/0120185 A1 | 8/2002 | Johnson | 600/345 |
| 2002/0143286 A1 | 10/2002 | Tumey | 604/11 |
| 2002/0161346 A1 | 10/2002 | Lockwood et al. | 604/315 |
| 2002/0183702 A1 | 12/2002 | Henley et al. | 604/305 |
| 2002/0193723 A1 | 12/2002 | Batdorf et al. | 602/48 |
| 2003/0032951 A1 | 2/2003 | Rittman et al. | 606/34 |
| 2003/0077311 A1 | 4/2003 | Vyakarnam et al. | 435/41 |
| 2003/0093041 A1 | 5/2003 | Risk, Jr. et al. | 604/308 |
| 2003/0143352 A1 | 7/2003 | Yang et al. | 428/36.9 |
| 2003/0208149 A1 | 11/2003 | Coffey | 602/48 |
| 2003/0219469 A1 | 11/2003 | Johnson et al. | 424/445 |
| 2004/0039415 A1 | 2/2004 | Zamierowski | 606/216 |
| 2004/0064111 A1 | 4/2004 | Lockwood et al. | 604/305 |
| 2004/0167482 A1 | 8/2004 | Watson | 604/317 |
| 2004/0243073 A1 | 12/2004 | Lockwood et al. | 604/313 |
| 2004/0249353 A1 | 12/2004 | Risks et al. | 604/315 |
| 2004/0260230 A1 | 12/2004 | Randolph | 604/28 |
| 2005/0033197 A1 | 2/2005 | Cottler | 600/573 |
| 2005/0065484 A1 | 3/2005 | Watson | 604/289 |
| 2005/0070858 A1 | 3/2005 | Lockwood et al. | 604/319 |
| 2005/0090787 A1 | 4/2005 | Risk et al. | 604/305 |
| 2005/0131327 A1 | 6/2005 | Lockwood et al. | 602/41 |
| 2005/0182446 A1 | 8/2005 | DeSantis | 606/222 |
| 2005/0234485 A1 | 10/2005 | Seegert et al. | 606/172 |
| 2006/0015087 A1 | 1/2006 | Risk et al. | 604/541 |
| 2006/0029650 A1 | 2/2006 | Coffey | 424/443 |
| 2006/0029675 A1 | 2/2006 | Ginther | 424/486 |
| 2006/0041247 A1 | 2/2006 | Petrosenko et al. | 604/543 |
| 2006/0079852 A1 | 4/2006 | Bubb | 604/317 |
| 2006/0129137 A1 | 6/2006 | Lockwood et al. | 604/543 |
| 2006/0149170 A1 | 7/2006 | Boynton et al. | 601/6 |
| 2006/0173253 A1 | 8/2006 | Ganapathy et al. | 600/310 |
| 2006/0189910 A1 | 8/2006 | Johnson et al. | 602/42 |
| 2006/0213527 A1 | 9/2006 | Argenta et al. | 128/898 |
| 2007/0005028 A1 | 1/2007 | Risk et al. | 604/315 |
| 2007/0014837 A1 | 1/2007 | Johnson et al. | 424/443 |
| 2007/0021697 A1 | 1/2007 | Ginther et al. | 602/1 |
| 2007/0021698 A1 | 1/2007 | Fleischmann | 602/2 |
| 2007/0032778 A1 | 2/2007 | Heaton et al. | 604/540 |
| 2007/0038172 A1 | 2/2007 | Zamierowski | 604/20 |
| 2007/0156104 A1 | 7/2007 | Lockwood et al. | 604/305 |
| 2007/0233022 A1 | 10/2007 | Henley et al. | 604/304 |
| 2009/0082740 A1 | 3/2009 | Lockwood et al. | 602/41 |
| 2010/0063483 A1 | 3/2010 | Adahan | 604/543 |

FOREIGN PATENT DOCUMENTS

| | | |
|---|---|---|
| AU | 745271 | 4/1999 |
| AU | 755496 | 2/2002 |
| CA | 1127488 | 7/1982 |
| CA | 2005436 | 6/1990 |
| CA | 2303085 | 3/1999 |
| DE | 0372727 | 3/1923 |
| DE | 2640413 A1 | 3/1978 |
| DE | 2809828 | 9/1978 |
| DE | 3102674 | 9/1982 |
| DE | 3539533 | 5/1987 |
| DE | 4012232 A1 | 10/1991 |
| DE | 4111122 | 4/1993 |
| DE | 4306478 A1 | 9/1994 |
| DE | 29504378 | 10/1995 |
| DE | 29715634 | 11/1997 |
| DE | 19722075 | 10/1998 |
| DK | 0064055 | 10/1945 |
| EP | 0 100 148 A1 | 2/1984 |
| EP | 0117632 | 9/1984 |
| EP | 0 161 865 A2 | 11/1985 |
| EP | 0 358 302 A2 | 3/1990 |
| EP | 0424165 | 4/1991 |
| EP | 0485657 | 5/1992 |
| EP | 0547496 | 6/1993 |
| EP | 0 730 845 | 9/1996 |
| EP | 0853950 | 7/1998 |
| EP | 077504 | 10/1998 |
| EP | 0880953 | 12/1998 |
| EP | 1088569 | 4/2001 |
| EP | 1100574 | 5/2001 |
| EP | 1 190 732 A1 | 3/2002 |
| EP | 1 018 967 B1 | 8/2004 |
| EP | 1726276 | 11/2006 |
| FR | 500253 | 3/1920 |
| FR | 1303238 | 7/1962 |
| GB | 3090 | 0/1902 |
| GB | 641061 | 8/1950 |
| GB | 692578 | 6/1953 |
| GB | 1549756 | 8/1979 |
| GB | 1584772 | 2/1981 |
| GB | 2195255 A | 4/1988 |
| GB | 2197789 A | 6/1988 |
| GB | 2220357 | 1/1990 |
| GB | 2235877 A | 3/1991 |
| GB | 2307180 | 5/1997 |
| GB | 2329127 | 3/1999 |
| GB | 2333965 | 8/1999 |
| GB | 2336546 | 10/1999 |
| GB | 2342584 | 4/2000 |
| GB | 2344531 | 6/2000 |
| GB | 2351025 | 12/2000 |
| GB | 2356148 A | 5/2001 |
| HU | 199304 | 1/1989 |
| HU | 51150 | 4/1990 |
| HU | 205557 | 4/1990 |
| HU | P9006526 | 1/1993 |
| HU | P9302966 | 7/1996 |
| HU | 76351 | 8/1997 |
| HU | 215563 | 8/1997 |
| HU | 1666 | 12/1999 |
| JP | 57-177758 | 11/1982 |
| JP | 4-129536 | 4/1992 |
| JP | H6-14995 | 1/1994 |
| JP | 6-327761 | 11/1994 |
| JP | H10-504484 | 5/1998 |
| JP | 2001-283352 | 10/2001 |
| JP | 2001-524850 | 12/2001 |
| SE | 0084485 | 10/1935 |
| SG | 71559 | 4/2002 |
| SU | 587041 | 1/1978 |
| SU | 1268175 | 11/1986 |
| WO | WO 80/02182 | 10/1980 |
| WO | WO 87/04626 | 8/1987 |
| WO | WO 89/04158 | 5/1989 |
| WO | WO 90/10424 | 9/1990 |
| WO | WO 90/11795 | 10/1990 |
| WO | WO 91/00718 | 1/1991 |
| WO | WO 91/08793 | 6/1991 |
| WO | WO 91/16030 | 10/1991 |
| WO | WO 92/12750 | 8/1992 |
| WO | WO 92/19313 | 11/1992 |
| WO | WO 92/20299 | 11/1992 |
| WO | WO 93/09715 | 3/1993 |
| WO | WO 93/09727 | 5/1993 |
| WO | WO 94/00090 | 1/1994 |
| WO | WO 94/20041 | 9/1994 |
| WO | WO 96/05873 | 2/1996 |
| WO | WO 96/50873 | 2/1996 |
| WO | WO 96/15745 | 5/1996 |
| WO | WO 97/18007 | 3/1997 |
| WO | WO 98/02205 | 1/1998 |
| WO | WO 98/38944 | 9/1998 |
| WO | WO 99/01173 | 1/1999 |
| WO | WO 99/13793 | 3/1999 |
| WO | WO 99/23990 | 5/1999 |
| WO | WO 99/59816 | 11/1999 |

| | | |
|---|---|---|
| WO | WO 00/07653 | 2/2000 |
| WO | WO 00/15277 | 3/2000 |
| WO | WO 00/21586 | 4/2000 |
| WO | WO 00/26100 | 5/2000 |
| WO | WO 00/28890 | 5/2000 |
| WO | WO 00/30567 | 6/2000 |
| WO | WO 00/32247 | 6/2000 |
| WO | WO 00/38552 | 7/2000 |
| WO | WO 00/38755 | 7/2000 |
| WO | WO 00/42958 | 7/2000 |
| WO | WO 00/59418 | 10/2000 |
| WO | WO 00/59424 | 10/2000 |
| WO | WO 00/61206 | 10/2000 |
| WO | WO 00/64394 | 11/2000 |
| WO | WO 01/34223 | 5/2001 |
| WO | WO 01/37922 | 5/2001 |
| WO | WO 01/49233 | 7/2001 |
| WO | WO 01/84931 | 11/2001 |
| WO | WO 01/85248 | 11/2001 |
| WO | WO 01/89431 | 11/2001 |
| WO | WO 02/38091 | 5/2002 |
| WO | WO 02/43634 | 6/2002 |
| WO | WO 03/005943 | 1/2003 |
| WO | WO 03/045492 | 6/2003 |
| WO | WO 03/057071 | 7/2003 |
| WO | WO 03/057307 | 7/2003 |
| WO | WO 03/101508 | 12/2003 |

OTHER PUBLICATIONS

Notice of Allowance issued in U.S. Appl. No. 10/524,957, mailed Oct. 14, 2010.
Notice of Allowance issued in U.S. Appl. No. 10/664,535, mailed Sep. 9, 2010.
Notice of Allowance issued in U.S. Appl. No. 11/242,543, mailed Sep. 27, 2010.
Notice of Allowance issued in U.S. Appl. No. 11/684,989, mailed Nov. 8, 2010.
Office Action issued in European Application No. 01 998 292.5, mailed May 7, 2010.
Office Action issued in European Application No. 02 794 397.6, mailed Oct. 12, 2010.
Office Action issued in Japanese Application No. 2008-007788, mailed Oct. 5, 2010.
Office Action issued in U.S. Appl. No. 11/051,283, mailed Oct. 15, 2010.
Office Action issued in U.S. Appl. No. 11/230,988, mailed Oct. 15, 2010.
Office Action issued in U.S. Appl. No. 11/515,983, mailed Oct. 5, 2010.
Response to Opposition submitted in European Patent No. EP 1 772 160, filed Sep. 29, 2010.
"Jump-Start Wound Healing with OASIS," *WOUNDS*, Special Supplement, 13(2):1-28, 2001.
"Oasis™ Wound Dressing," *SIS™ Technology*, pp. 1-4, Sep. 2001.
"Surgisis™ Soft-Tissue Graft," *SIS™ Technology*, pp. 1-4, Sep. 2001.
Abdullah, BJJ, JHK Coll Radiol, Feb. 21, 2001; vol. 4, pp. 272-273—"A New Method for Fixation of Drainage Catheters."
Agenta et al., "Vacuum-assisted closure: A new method for wound control and treatment," *Annals of Plastic Surgery*, 38(6), 1997.
Arnljots and Svedman, "Irrigation Treatment in Split-Thickness Skin Grafting of Intractable Leg Ulcers," *Scand J. Plast Reconstr. Surg.*, 19(2):211-213, 1985.
Bagautdinov, "Variant of external vacuum aspiration in the treatment of purulent diseases of soft tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).
Blackburn II et al.; "Negative-pressure dressings as a bolster for skin grafts," *Annals of Plastic Surgery*, 40(5):453-457, 1998.
Brochure—"Cavi-Care," *Smith & Nephew*, 2000.
Brochure—Aeros—Care-E-Vac; 2 pages.
Brochure—Aeros—Instavac Aspirator, 1 page.
Brochure—Augustine Medical, Warm-up Active Wound Therapy Wound Covers, 1999; 3 pages.
Brochure—Emerson Transport Suction Unit; 1 page.
Brochure—Healthpoint® Oasis® Wound Matrix, *Cook Biotech Incorporated*, 2003.
Brochure—Hiblow Air Pump; 1 page.
Brochure—KCI—The V.A.C. (Vacuum Assisted Closure), Nov. 5, 1998; 7 pages.
Brochure—Microtek Heritage, Inc.—The Wound-Evac ET, Closed Wound Suction System; 4 pages.
Brochure—Pleur-evac Adult-Pediatric-Non-Metered Disposable "3-Bottle" Unit, A-4000; 6 pages.
Brochure—Series 55—Emerson Post-Operative Suction Pumps; 1 page.
Brochure—Wells Johns Company—Point 5 Aspirator, 2 pages.
Brochure/Instruction manual—Creative Medical Laboratories, Inc.—TUGS (Transportable Universal Gradient Suction) System.
Brozov et al., *Vestn. Dermatol. Venerol.*, Aug. 1965—"Vacuum therapy of some skin diseases," (English translation by R. McElroy Translation Co., Austin, Texas).
Bucalo et al., "Inhibition of cell proliferation by chronic wound fluid," *Wound Repair and Regeration*, pp. 181-186, Jul.-Sep. 1993.
Chariker et al., "Effective management of incisional and cutaneous fistulae with closed suction wound drainage," *Contemporary Surgery*, 34:59-63, 1989.
Chinn and Burns, "Closed wound suction drainage," *The Journal of Foot Surgery*, 24(1):76-81, 1985.
Comment-Dunlop et al., Apr. 1991, pp. 505-506 on "Vaccuum drainage of groin wounds after facular surgery."
Comment-Ruckley et al., "Vacuum drainage of groin wounds after vascular surgery," pp. 505-506, 1991.
Dattilo, Jr. et al.; "Medical textiles: application of an absorbable barbed bi-directional surgical suture"; *Journal of Textile and Apparel, Technology and Management*, 2(2):1-5, 2002.
Davydov et al., "Concepts for the clinical-biological management of the wound process in the treatment of purulent wounds by means of vacuum therapy," *Vestnik Khirurgi*, pp. 132-136 (and 8 page English translation thereof), Jul. 1980.
Davydov et al., *Khirurgiia*, Jun. 1990—"Pathogenic Mechanism of the Effect of Vacuum Therapy on the course of the wound process" (English translation by R. McElroy Translation Co., Austin, Texas).
Davydov et al., *Vesn. Khir.*, Sep. 1988—"Vacuum Therapy in the Treatment of Acute Suppurative Disease of Soft Tissues and Suppurative Wounds" (English translation by R. McElroy Translation Co., Austin, Texas).
Davydov et al., *Vestn. Khir.*, Mar. 1990—"Basis of the Use of Forced Early Secondary Suture in the Treatment of Suppurative Wounds" (English translation by R. McElroy Translation Co., Austin, Texas).
Davydov et al., *Vestn. Khir.*, Nov. 1986—"Vacuum Therapy in the Treatment of Suppurative lactation Mastitis," (English translation by R. McElroy Translation Co., Austin, Texas).
Dunlop et al., "Vaccum drainage of groin wounds after vascular surgery: A controlled trial," *Br. J. Surg.*, 77:562-563, 1990.
Egnell Minor, Instruction Book, First Edition, 300, 7502, pp. 24, Feb. 1975.
Egnell Minor: Addition to the Users Manual Concerning Overflow Protection—Concerns all Egnell Pumps, Feb. 3, 1983, pp. 2.
European Search Report dated May 3, 2007 for EP Appln. No. 07001838.2-2310.
European Search Report issued in connection with European Application No. 07001838.7.
Fleischmann, "Vacuum sealing for treatment of problematic wounds" *WundForum Spezial IHW*, pp. 54-55, 1994.
Fleishman et al., "Vacuum sealing for treatment of soft tissue injury in open fractures," *Unfallchirurg*, 96:488-492, 1993. (English translation of the Summary provided).
Fourth SIS-ECM Symposium, Phoenix, Arizona, Dec. 6-7, 2002.
Genecov et al., "A Controlled subatomspheric pressure dressing increases ther ate of skin graft donor site reepithelialization," *Annals of Plastic Surgery*, 40(3):219-225, 1998.
Greer et al., "The use of subatmospheric pressure dressing therapy to close lymphocutaneous fistulas of the groin," *British Journal of Plastic Surgery*, 53(6):484-487, 2000.

International Search Report for WO 03/045492 A1, Lockwood et al., Jun. 2003.
International Search Report for Wo 2003/045492 A1, Lockwood et al., Jun. 2003.
Jeter et al., *Chronic Wound Care*, 27: p. 240-246—"Managing draining wounds and fistulae: New and established Methods."
Johnson, "An improved technique for skin graft placement using a suction drain," *Surgery, Gynecology, and Obstetrics*, 159(6):584-585, 1984.
Kinetic Concepts, Inc., Form 10-K—Annual report pursuant to section 13 or 15(d) of the Securities Exchange Act of 1934, for the fiscal year ended Dec. 31, 2006, United States Securities and Exchange Commission, pp. 1, 2, 3, 12, 13, and 14.
Klein, "Cook Incorporated forms dedicated tissue engineered products group," *PR Newswire*, 2000.
Kostluchenok et al., "Vacuum treatment in the surgical treatment of suppurative wounds," *Vestn. Khir.*, Sep. 1986. (English translation by R. McElroy Translation Co., Austin, Texas).
Kuznetsov and Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92, Oct. 1986.
Landis et al., "Alternate suction and pressure," pp. 925-961—"The effects of alternative suction and pressure on blood flow to the lower extremities."
Letsou et al., "Stimulation of adenylate cyclase activity in cultured endothelial cells subjected to cyclic stretch," *Journal of Cardiovascular Surgery*, 31:634-639, 1990.
Letter and Memo reporting Office Action issued in Mexican Application No. PA/a/2001/001124, mailed Jul. 13, 2004.
Lundvall et al., "Transmission of externally applied negative pressure to the underlying tissue: A study on the upper arm of man," *Acta. Physiol. Scand.*, 136:403-409, 1989.
Masters, "Reliable, inexpensive and simple suction dressings," Letter to the Editor, *British Journal of Plastic Surgery*, Elsevier Science/The British Association of Plastic Surgeons, UK, 51(3):267, 1998.
McCarty, "Cook Incorporated forms dedicated tissue engineered products group," *Cook® Online, News and Media Information*, 2000.
Medical Industry Week—article "KCI Offers New Treatment for Non-Healing Wounds," 1 page.
Mendez-Eastman, "When wounds won't heal," *RN*, 61(1):20-24, 1998.
Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.
Mizazimov et al., *Ortop Travmatol Protez.*, Oct. 1966—"Free skin graft of the foot with preparation of the wounded surface by vacuum treatment" (English translation by R. McElroy Translation Co., Austin, Texas).
Morykwas et al., "Nonsurgical modalities to enhance healing and care of soft tissue wounds," http://www.sma.org.soa.jsoawt97, 16 pages, Feb. 11, 2999.
Morykwas et al., "Use of Negative Pressure to increase the Rate of Granulation Tissue Formation in Chronic Open Wounds," *Extracellular Matric and Healing*, pp. 800, 1993.
Morykwas et al., "Vacuum-assisted closure: A new method for wound control and treatment: Animal studies and basic foundation," *Annals of Plastic Surgery*, 38(6), 1997.
Mulder et al., "Clinicians Pocket Guide to Chronic Wound Repair," *Wound Healing Publications*, 1991.
Nakayama et al., "A new dressing method for free skin grafting in hands," *Ann. Plast. Surg.*, 26(5):499-502, May 1991.
Nakayama et al., A new method for the dressing of free skin grafts, *Plast. Reconstr. Surg.*, 86(6):1216-1219, 1990.
Nueman et al., "Gelatin-based sprayable foam as a skin substitute," *J. Biomed. Materials Research*, 15:9-18, 1981.
Office Action dated Jan. 10, 2007 for U.S. Appl. No. 10/509,137, filed Sep. 27, 2004.
Office Action dated Oct. 26, 2007 for U.S. Appl. No. 11/051,283, filed Feb. 4, 2005.
Office Action dated Mar. 13, 2007 for U.S. Appl. No. 11/230,988, filed Sep. 20, 2005.
Office Action dated Mar. 22, 2007 for U.S. Appl. No. 11/051,283, filed Feb. 4, 2005.
Office Action dated Jun. 22, 2007 for U.S. Appl. No. 10/209,137, filed Sep. 27, 2004.
Office Action dated Sep. 10, 2007 for U.S. Appl. No. 11/230,988, filed Sep. 20, 2005.
Office Action dated Sep. 28, 2006 for U.S. Appl. No. 11/230,988, filed Sep. 20, 2005.
Office Action dated Sep. 29, 2006 for U.S. Appl. No. 11/051,283, filed Feb. 4, 2005.
Office Action dated Sep. 7, 2005 for U.S. Appl. No. 11/051,283, filed Feb. 4, 2005.
Office Action dated Sep. 7, 2007 for U.S. Appl. No. 11/051,283, filed Feb. 4, 2005.
Office Action issued in Australian Application No. 5255/99, mailed Aug. 6, 2002.
Office Action issued in Canadian Application No. 2,338,443, mailed Feb. 7, 2006.
Office Action issued in Canadian Application No. 2,390,131, mailed Jul. 20, 2007.
Office Action issued in Canadian Application No. 2,467,837, mailed May 27, 2009.
Office Action issued in Canadian Application No. 2,481,016, mailed Aug. 13, 2009.
Office Action issued in Czech Republic Application No. PV2001-497, mailed Feb. 7, 2001.
Office Action issued in European Application No. 00991498.7, mailed Dec. 17, 2003.
Office Action issued in European Application No. 00991498.7, mailed Jan. 2, 2006.
Office Action issued in European Application No. 01998292.5, mailed Feb. 18, 2005.
Office Action issued in European Application No. 01998292.5, mailed Jul. 17, 2006.
Office Action issued in European Application No. 01998292.5, mailed Sep. 12, 2008.
Office Action issued in European Application No. 02784588.2, mailed Sep. 15, 2005.
Office Action issued in European Application No. 08010957.2, mailed Apr. 8, 2009.
Office Action issued in European Application No. 99 937 799, mailed Aug. 18, 2003.
Office Action issued in Japanese Application No. 2004-508861, mailed Apr. 14, 2009, and English language translation thereof.
Office Action issued in Polish Application No. P-357 417, mailed Nov. 25, 2008; English translation.
Office Action issued in Polish Application No. P-364 754, 2006.
Office Action issued in U.S. Appl. No. 09/369,113, mailed Jan. 31, 2001.
Office Action issued in U.S. Appl. No. 09/725,352, mailed Dec. 12, 2002.
Office Action issued in U.S. Appl. No. 09/743,737, mailed Aug. 11, 2006.
Office Action issued in U.S. Appl. No. 09/743,737, mailed Apr. 1, 2003.
Office Action issued in U.S. Appl. No. 09/743,737, mailed Jun. 19, 2002.
Office Action issued in U.S. Appl. No. 09/743,737, mailed Oct. 23, 2002.
Office Action issued in U.S. Appl. No. 09/743,737, mailed Sep. 8, 2005.
Office Action issued in U.S. Appl. No. 09/855,287, mailed Dec. 15, 2003.
Office Action issued in U.S. Appl. No. 09/855,287, mailed Jul. 14, 2005.
Office Action issued in U.S. Appl. No. 09/855,287, mailed Jun. 24, 2004.
Office Action issued in U.S. Appl. No. 09/855,287, mailed Oct. 1, 2002.
Office Action issued in U.S. Appl. No. 09/994,537, mailed Jan. 16, 2003.

Office Action issued in U.S. Appl. No. 09/994,537, mailed Jun. 30, 2003.
Office Action issued in U.S. Appl. No. 10/144,504, mailed May 14, 2004.
Office Action issued in U.S. Appl. No. 10/267,358, mailed Jun. 29, 2005.
Office Action issued in U.S. Appl. No. 10/276,778, mailed Aug. 7, 2008.
Office Action issued in U.S. Appl. No. 10/276,778, mailed Apr. 24, 2006.
Office Action issued in U.S. Appl. No. 10/276,778, mailed Jul. 13, 2007.
Office Action issued in U.S. Appl. No. 10/276,778, mailed Mar. 22, 2007.
Office Action issued in U.S. Appl. No. 10/276,778, mailed Nov. 19, 2007.
Office Action issued in U.S. Appl. No. 10/276,778, mailed Oct. 11, 2006.
Office Action issued in U.S. Appl. No. 10/496,360, mailed Jun. 2, 2009.
Office Action issued in U.S. Appl. No. 10/496,360, mailed Jun. 12, 2006.
Office Action issued in U.S. Appl. No. 10/496,360, mailed Mar. 26, 2008.
Office Action issued in U.S. Appl. No. 10/496,360, mailed Mar. 14, 2007.
Office Action issued in U.S. Appl. No. 10/496,360, mailed Oct. 3, 2008.
Office Action issued in U.S. Appl. No. 10/496,360, mailed Oct. 5, 2006.
Office Action issued in U.S. Appl. No. 10/496,360, mailed Sep. 10, 2007.
Office Action issued in U.S. Appl. No. 10/496,623, mailed Jun. 9, 2006.
Office Action issued in U.S. Appl. No. 10/509,137, mailed Dec. 20, 2007.
Office Action issued in U.S. Appl. No. 10/509,137, mailed Jun. 3, 2009.
Office Action issued in U.S. Appl. No. 10/509,137, mailed Nov. 24, 2008.
Office Action issued in U.S. Appl. No. 10/524,957, mailed Apr. 11, 2007.
Office Action issued in U.S. Appl. No. 10/524,957, mailed Apr. 15, 2008.
Office Action issued in U.S. Appl. No. 10/524,957, mailed Aug. 10, 2007.
Office Action issued in U.S. Appl. No. 10/524,957, mailed Aug. 3, 2009.
Office Action issued in U.S. Appl. No. 10/524,957, mailed Sep. 30, 2008.
Office Action issued in U.S. Appl. No. 10/664,535, mailed Apr. 2, 2007.
Office Action issued in U.S. Appl. No. 10/664,535, mailed Apr. 17, 2008.
Office Action issued in U.S. Appl. No. 10/664,535, mailed Dec. 15, 2009.
Office Action issued in U.S. Appl. No. 10/664,535, mailed Mar. 1, 2006.
Office Action issued in U.S. Appl. No. 10/664,535, mailed Mar. 26, 2007.
Office Action issued in U.S. Appl. No. 10/664,535, mailed Oct. 16, 2006.
Office Action issued in U.S. Appl. No. 10/885,431, mailed Apr. 15, 2008.
Office Action issued in U.S. Appl. No. 10/885,431, mailed Jun. 24, 2009.
Office Action issued in U.S. Appl. No. 10/885,431, mailed Mar. 22, 2007.
Office Action issued in U.S. Appl. No. 10/885,431, mailed Sep. 26, 2008.
Office Action issued in U.S. Appl. No. 10/885,431, mailed Sep. 19, 2007.
Office Action issued in U.S. Appl. No. 10/885,431, mailed Sep. 11, 2006.
Office Action issued in U.S. Appl. No. 10/997,612, mailed Apr. 30, 2007.
Office Action issued in U.S. Appl. No. 10/997,612, mailed Mar. 20, 2008.
Office Action issued in U.S. Appl. No. 10/997,612, mailed May 5, 2006.
Office Action issued in U.S. Appl. No. 10/997,612, mailed Nov. 14, 2008.
Office Action issued in U.S. Appl. No. 10/997,612, mailed Nov. 19, 2007.
Office Action issued in U.S. Appl. No. 10/997,612, mailed Oct. 31, 2006.
Office Action issued in U.S. Appl. No. 11/051,283, mailed Feb. 22, 2006.
Office Action issued in U.S. Appl. No. 11/051,283, mailed Jun. 5, 2009.
Office Action issued in U.S. Appl. No. 11/051,283, mailed Jan. 9, 2008.
Office Action issued in U.S. Appl. No. 11/051,283, mailed Oct. 17, 2008.
Office Action issued in U.S. Appl. No. 11/230,988, mailed Apr. 16, 2009.
Office Action issued in U.S. Appl. No. 11/230,988, mailed Aug. 26, 2009.
Office Action issued in U.S. Appl. No. 11/230,988, mailed Mar. 26, 2008.
Office Action issued in U.S. Appl. No. 11/230,988, mailed Oct. 3, 2008.
Office Action issued in U.S. Appl. No. 11/242,543, mailed May 18, 2007.
Office Action issued in U.S. Appl. No. 11/242,543, mailed Oct. 20, 2006.
Office Action issued in U.S. Appl. No. 11/242,543, mailed Oct. 25, 2007.
Office Action issued in U.S. Appl. No. 11/347,073, mailed Apr. 1, 2008.
Office Action issued in U.S. Appl. No. 11/515,983, mailed May 11, 2009.
Office Action issued in U.S. Appl. No. 11/684,989, mailed Jul. 7, 2009.
Office Action issued in U.S. Appl. No. 11/684,989, mailed Nov. 18, 2008.
Office Action issued in U.S. Appl. No. 11/761,066, mailed Dec. 13, 2007.
Office Action issued in U.S. Appl. No. 11/761,066, mailed Jun. 2, 2009.
Office Action issued in U.S. Appl. No. 11/761,066, mailed Oct. 28, 2008.
Office Action issued in U.S. Appl. No. 11/761,066, mailed Sep. 25, 2007.
Olenius et al., "Mitotic activity in expanded human skin," *Plastic and Reconstructive Surgery*, pp. 213-215, 1993.
One page brochure—Aeros—MobilvacII.
Orringer et al., "Management of wounds in patients with complex enterocutaneous fistulas," *Surgery, Gynecology & Obstetrics*, 165:79-80, 1987.
Osterbroek et al., "A micromachined pressure/flow-sensor" (Abstract only), www.ingentraconnect.com/content/els/09244247/1999/00000077/art00188, *Sensor and Actuators*, A: vol. 77, No. 3, Nov. 2, 1999.
Patent Application and Drawings—"Method of treating tissue damage and apparatus for same," consisting of 28 pages.
Patent Application and Drawings—"The enhancement of wound healing and flap survival by a new negative pressure device," Argenta et al., consisting of 30 pages.
PCT Declaration of Non-Establishment of International Search Report issued in International Application No. PCT/US2003/17099, mailed Nov. 7, 2003.
PCT International Preliminary Examination Report dated Dec. 3, 2003 for PCT/US01/44194 filed Nov. 27, 2001.

PCT International Preliminary Examination Report issued in International Application No. PCT/GB1996/02802, mailed Jan. 15, 1998.
PCT International Preliminary Examination Report issued in International Application No. PCT/US1999/17877, mailed Oct. 30, 2001.
PCT International Preliminary Examination Report issued in International Application No. PCT/US2000/42333, mailed Nov. 19, 2002.
PCT International Preliminary Search Report dated Jul. 4, 2003 for PCT/US02/37814 filed Nov. 25, 2002.
PCT International Search Report issued in International Application No. PCT/GB1995/01983, mailed Nov. 23, 1995.
PCT International Search Report issued in International Application No. PCT/GB1996/02802, mailed Apr. 29, 1997.
PCT International Search Report issued in International Application No. PCT/GB1998/02713, mailed Jan. 8, 1999.
PCT International Search Report issued in International Application No. PCT/US1999/17877, mailed Oct. 27, 1999.
PCT International Search Report issued in International Application No. PCT/US2000/42333, mailed Aug. 3, 2001.
PCT International Search Report issued in International Application No. PCT/US2001/15611, mailed Sep. 5, 2001.
PCT International Search Report issued in International Application No. PCT/US2001/44194, mailed Dec. 9, 2002.
PCT International Search Report issued in International Application No. PCT/US2002/32221, mailed Feb. 5, 2003.
PCT International Search Report issued in International Application No. PCT/US2002/41210, mailed Oct. 28, 2003.
PCT International Search Report issued in International Application No. PCT/US2002/41228, mailed Jun. 30, 2003.
PCT International Search Report issued in International Application No. PCT/US2002/41229, mailed Jun. 30, 2003.
PCT International Search Report issued in International Application No. PCT/US2002/41231, mailed May 9, 2003.
PCT International Search Report issued in International Application No. PCT/US2002/41234, mailed Oct. 24, 2003.
PCT International Search Report issued in International Application No. PCT/US2002/41300, mailed Jul. 31, 2003.
PCT Written Opinion issued in International Application No. PCT/GB1996/02802, mailed Sep. 3, 1997.
PCT Written Opinion issued in International Application No. PCT/GB1998/02713, mailed Jun. 8, 1999.
PCT Written Opinion issued in International Application No. PCT/US1999/17877, mailed Aug. 20, 2001.
PCT Written Opinion issued in International Application No. PCT/US2000/42333, mailed Jun. 24, 2002.
Roget's New Millenium Thesaurus First Edition (V1.2.1), 2007.
Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R. 1967) (certified translation).
Sames, "Sealing of wounds with vacuum drainage," *Br. Med. J.*, 2(6096):1123, 1977.
Schein et al., "The 'Sandwich Technique' in the management of the open abdomen," *British Journal of Surgery*, 73:369-370, 1986.
Schneider et al., "A new and reliable method of securing skin grafts to the difficult recipient bed," *Plastic and Reconstructive Surgery*, pp. 1195-1198, 1998.
Search Report issued in Hungarian Application No. P0103545, mailed Oct. 29, 2001.
Search Report issued in Hungarian Application No. P0500055, mailed May 3, 2005.
Solovev et al., "Guidelines, the method of treatment of immature external fistulas in the upper gastrointestinal tract," editor-in-chief Prov. V.I. Parahonyak, S.M. Kirov Gorky State Medical Institute, Gorky, U.S.S.R., 1987.
Solovev, Dissertation Abstract, "Treatment and prevention of suture failures after gastric resection," S.M. Kirov Gorky State Medical Institute, Gorky, U.S.S.R., 1988.
Supplementary Search Report issued in European Application No. 02794388.5, mailed Jun. 16, 2009.
Supplementary Search Report issued in European Application No. 02794392.7, mailed Jun. 5, 2009.
Supplementary Search Report issued in European Application No. 02794393.5, mailed Aug. 1, 2006.
Supplementary Search Report issued in European Application No. 02794394.3, mailed Apr. 6, 2009.
Supplementary Search Report issued in European Application No. 02794397.6, mailed Jan. 29, 2009.
Supplementary Search Report issued in European Application No. 02796039.2, mailed Sep. 4, 2009.
Supplementary Search Report issued in European Application No. 08010957.2, mailed Aug. 27, 2008.
Svedman et al., "A dressing system providing fluid supply and suction drainage used for continuous or intermittent irrigation," *Annals of Plastic Surgery*, 17(2):125-133, 1989.
Svedman, "A dressing allowing continuous treatment of a biosurface," *IRCS Medical Science: Biomedical Technology, Clinical Medicine, Surgery and Transplantation*, 7:221, 1979.
Svedman, "Irrigation treatment of leg ulcers," *The Lancet*, 2(8349):532-534, 1983.
Teder et al., "Continous wound irrigation in the pig," *J. Invest. Surg.*, 3:399-407, 1990.
Tennant, "The use of hypermia in the postoperative treatment of lesions of the extremities and thorax," *Journal of the American Medical Association*, 64:1548-1549, 1915.
Tittel et al., "New standards in postoperative wound drainage," *Eingag und Annahme das Manuskripts*, pp. 104-107, Jan. 7, 1987.
Tribble, "An improved sump drain-irrigation device of simple construction," *Archives of Surgery*, 105(3):511-513, 1972.
Valenta, "Using the vacuum dressing alternative for difficult wounds," *AIN*, pp. 44-45, 1994.
Viljanto et al., "Local hyperalimentation of open wounds" *Br. J. Surg.*, 63:427-430, 1976.
Walthuis et al., "Physiological effects of locally applied reduced pressure in man," *Physiological Reviews*, 54(3):566-595, 1974.
Wood et al., "Foam elastomer dressing in the management of open granulating wounds: Experience with 250 patients," *Br. J. of Surg.*, 64:554-557, 1977.
Wooding-Scott et al., "No wound is too big for resourceful nurses," *RN*, pp. 22-25, 1988.
Yusupov et al., "Active wound drainage," *Vestnik Khirurgi*, 138(4) (and 7 page English translation thereof), 1987.
Živadinović et al., "Vacuum therapy in the treatment of peripheral blood vessels," *Timok Medical Journal*, 11:161-164 (and certified translation), 1986.
Advisory Action issued in U.S. Appl. No. 10/885,431, mailed Dec. 8, 2009.
Advisory Action issued in U.S. Appl. No. 11/515,983, mailed Feb. 1, 2010.
Advisory Action issued in U.S. Appl. No. 11/761,066, mailed Feb. 16, 2010.
Decision on Appeal issued in U.S. Appl. No. 10/276,778, mailed Mar. 6, 2010.
Decision on Appeal issued in U.S. Appl. No. 11/242,543, mailed Mar. 5, 2010.
Definition of "pore," provided by Merriam-Webster Online Dictionary, printed Apr. 5, 2010.
Definition of "porous," provided by Merriam-Webster Online Dictionary, printed Apr. 5, 2010.
Office Action issued in U.S. Appl. No. 10/509,137, mailed Apr. 9, 2010.
Office Action issued in U.S. Appl. No. 10/524,957, mailed Feb. 25, 2010.
Office Action issued in U.S. Appl. No. 11/051,283, mailed Feb. 25, 2010.
Office Action issued in U.S. Appl. No. 11/515,983, mailed Nov. 20, 2009.
Office Action issued in U.S. Appl. No. 11/684,989, mailed Dec. 29, 2009.
Office Action issued in U.S. Appl. No. 11/761,066, mailed Dec. 9, 2009.
Advisory Action issued in U.S. Appl. No. 10/509,137, mailed Jun. 24, 2010.
Advisory Action issued in U.S. Appl. No. 11/051,283, mailed May 5, 2010.
Communication of Notice of Opposition issued in European Application No. 07001838.7, mailed Apr. 28, 2010 (Opposition).

Notice of Allowance issued in U.S. Appl. No. 10/276,778, mailed May 21, 2010.
Notice of Allowance issued in U.S. Appl. No. 10/664,535, mailed Jun. 2, 2010.
Notice of Allowance issued in U.S. Appl. No. 10/885,431, mailed Mar. 22, 2010.
Notice of Allowance issued in U.S. Appl. No. 11/761,066, mailed May 13, 2010.
Office Action issued in Canadian Application No. 2,481,016, mailed Jun. 15, 2010.
Office Action issued in Japanese Application No. 2001-539532, mailed May 11, 2010 (and English language translation thereof).
Office Action issued in Japanese Application No. 2004-508861, mailed Feb. 16, 2010 (and English language translation thereof).
Office Action issued in U.S. Appl. No. 10/524,957, mailed Jul. 26, 2010.
Office Action issued in U.S. Appl. No. 11/230,988, mailed May 26, 2010.
Office Action issued in U.S. Appl. No. 11/515,983, mailed May 7, 2010.
Office Action issued in U.S. Appl. No. 11/684,989, mailed Jun. 29, 2010.
Supplemental Notice of Allowability issued in U.S. Appl. No. 10/885,431, mailed Apr. 22, 2010.
Notice of Allowance issued in U.S. Appl. No. 11/051,283, mailed Mar. 29, 2011.
Notice of Allowance issued in U.S. Appl. No. 11/230,988, mailed Dec. 3, 2010.
Notice of Allowance issued in U.S. Appl. No. 11/515,983, mailed May 17, 2011.
Office Action issued in Canadian Application No. 2,481,016, mailed Apr. 1, 2011.
Office Action issued in European Application No. 02 794 388.5, mailed Feb. 10, 2011.
Office Action issued in European Application No. 02 794 392.7, mailed May 3, 2011.
Office Action issued in European Application No. 02 794 394.3, mailed Nov. 26, 2010.
Office Action issued in European Application No. 02 794 394.3, mailed Jun. 14, 2011.
Office Action issued in European Application No. 03 734 294.6, mailed Apr. 21, 2011.
Office Action issued in Japanese Application No. 2008-007788, mailed Jun. 28, 2011. (English translation).
Office Action issued in U.S. Appl. No. 10/509,137, mailed Dec. 8, 2010.
Office Action issued in U.S. Appl. No. 10/509,137, mailed Apr. 28, 2011.
Office Action issued in U.S. Appl. No. 12/328,531, mailed Jun. 13, 2011.
Office Action issued in U.S. Appl. No. 12/860,581, mailed Apr. 29, 2011.
Office Communication, issued in Japanese Patent Application No. 2009-236963, dated Aug. 2, 2011. (English translation).
Notice of Allowance issued in U.S. Appl. No. 10/509,137, dated Dec. 7, 2011.
Office Communication issued in Canadian Patent Application No. 2,689,308, dated Dec. 19, 2011.
Office Communication issued in European Patent Application No. 01 998 292.5, dated Feb. 16, 2002.
Office Communication issued in U.S. Appl. No. 12/328,531, dated Jan. 6, 2012.
Office Communication issued in U.S. Appl. No. 12/328,531, dated Mar. 16, 2012.
Office Communication issued in U.S. Appl. No. 12/860,581, dated Nov. 3, 2011.
Office Communication issued in U.S. Appl. No. 12/860,581, dated Jan. 18, 2012.
Office Communication issued in U.S. Appl. No. 12/860,581, dated Feb. 24, 2012.
US 6,216,701, 04/2001, Heaton et al. (withdrawn)

* cited by examiner

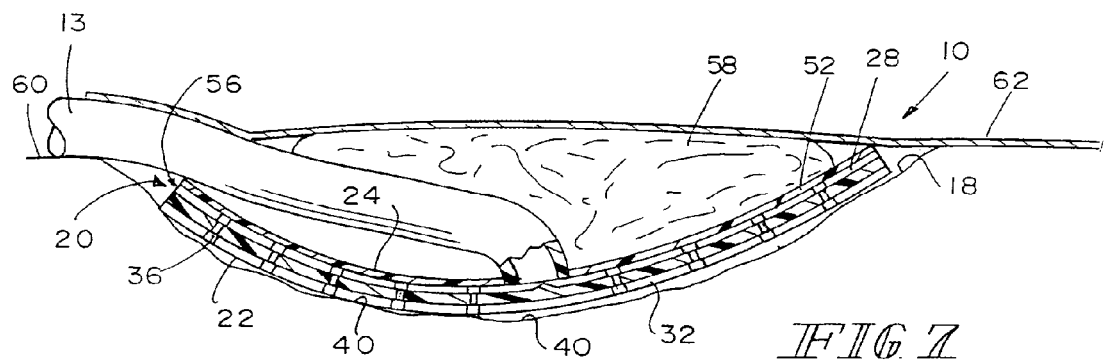
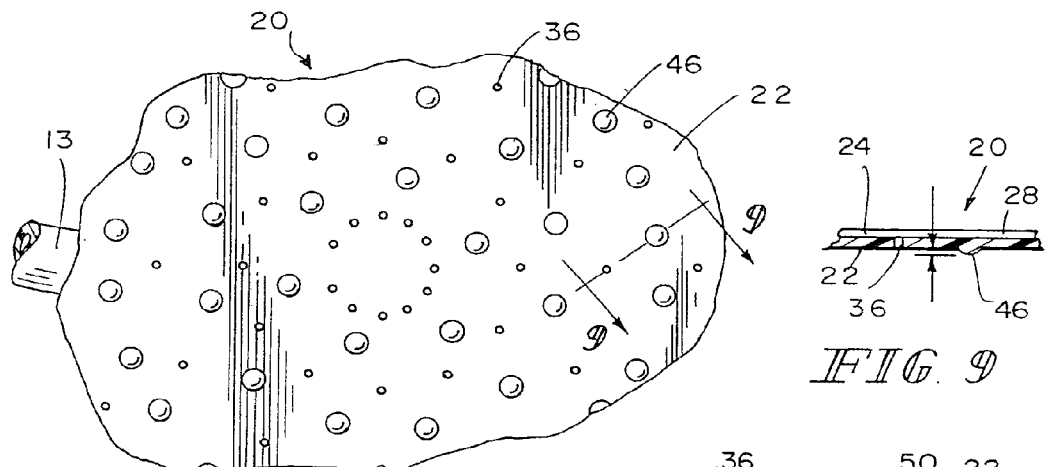
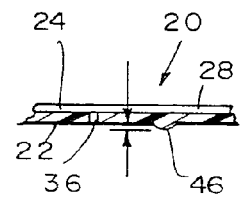
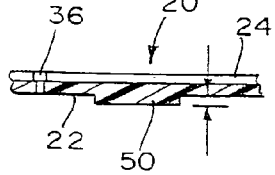
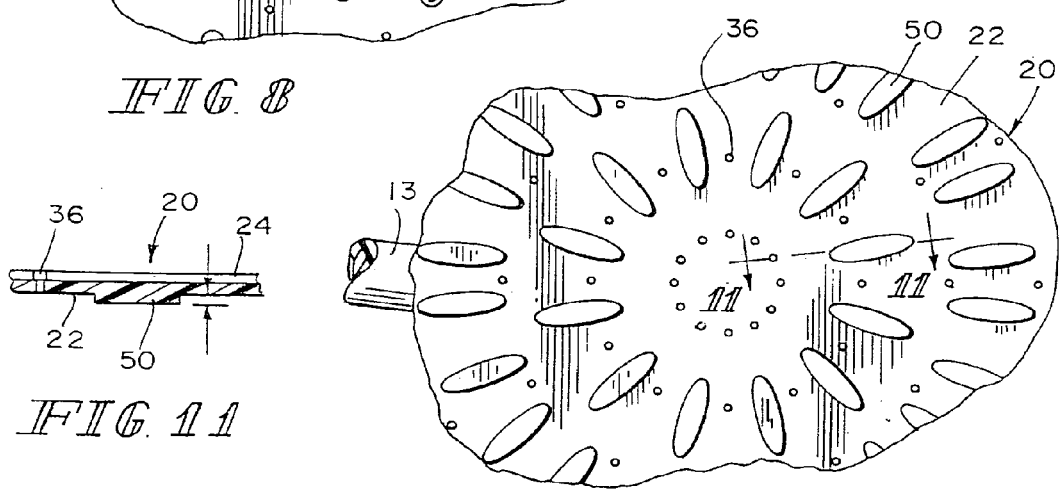

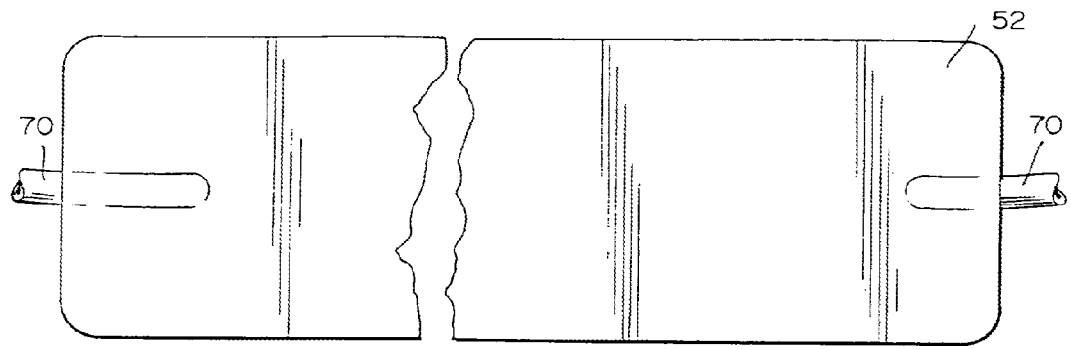
FIG. 12
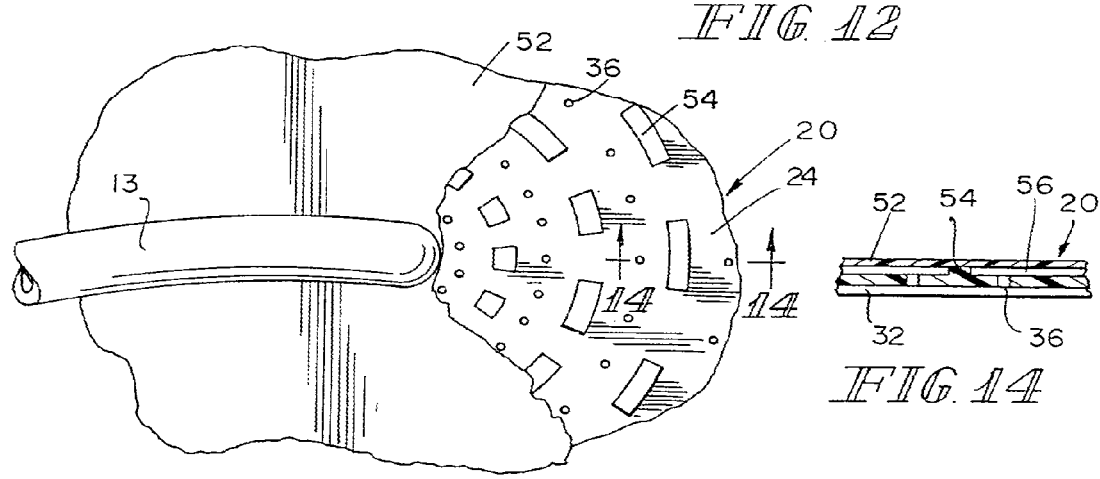
FIG. 13
FIG. 14
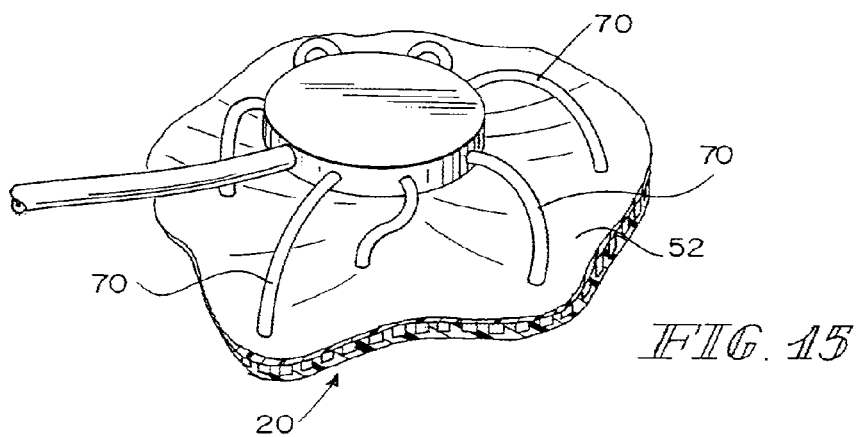
FIG. 15

VACUUM THERAPY AND CLEANSING DRESSING FOR WOUNDS

CROSS-REFERENCE TO RELATED APPLICATIONS

This application is a continuation of, and claims priority to U.S. patent application Ser. No. 10/664,535, filed Sep. 19, 2003; which is a divisional of, and claims priority to, U.S. patent application Ser. No. 09/725,352, filed Nov. 29, 2000, now issued as U.S. Pat. No. 6,685,681; both of which are incorporated by referenced in their entireties.

The present invention relates to bandages for wounds, and more particularly to the provision of bandages for use with a vacuum source.

BACKGROUND AND SUMMARY OF THE INVENTION

The prior art contemplates that chronic wounds may be treated by providing a vacuum in the space above the wound to promote healing.

A number of prior art references teach the value of the vacuum bandage or the provision of the vacuum in the space above the surface of a chronic wound. Several Russian language articles exist which establish the efficacy of vacuum therapy discovered in the 1980s. Examples of such prior art articles, each of which discusses the use of application of vacuum to a wound to promote healing, are as follows: "Vacuum therapy in the treatment of acute suppurative diseases of soft tissues and suppurative wounds", Davydov, et al., Vestn, Khir., Sept. 1988 ("The September 1988 article"); "Pathenogenic mechanism of the effect of vacuum therapy on the course of the wound process", Davydov, et al. Khirurigiia, June 1990 ("the June 1990 article"); and "Vacuum therapy in the treatment of suppurative lactation mastitis", Davydov, et al. Vestn. Khir., November 1986 ("the November 1986 article"). The Russian articles distinguish wound drainage from use of vacuum therapy for healing. The Russian authors report that vacuum therapy resulted in faster cleansing of the wound and more rapid detoxification than with the traditional incision-drainage method. The November 1986 Russian article describes the vacuum therapy techniques as a reduction of 0.8-1atmosphere for 20 minutes at the time of surgery, and subsequent 1.5 to 3 hour treatments at a reduced pressure of 0.1 to 0.15 from atmosphere, twice daily. These Russian articles teach the use of negative pressure to effect healing. The articles describe using several sessions per day, each lasting up to one hour, with a vacuum of 76 -114 mmHg. The Russian articles teach using this vacuum method to decrease the number of microbes in the wound. The June 1990 Russian article teaches that this vacuum therapy provides a significant antibacterial effect. The article describes the stepped up inflow of blood to the zone around the wound to lead to an increase in the number of leukocytes reaching the focus of inflammation. Subsequent articles and patents further develop the benefits obtained with vacuum therapy. The prior art, therefore, teaches the benefit and value of a vacuum bandage.

A vacuum bandage is a bandage having a cover which seals about the outer perimeter of the wound and under which a vacuum is established to act on the wound surface. This vacuum applied to the wound surface causes healing of chronic wounds. Typically, suction tubes are provided for drawing away exudate from the wound, and this suction may be used to create the vacuum under the cover. If the cover is a flexible cover, which is typically more comfortable for the patient, some sort of porous packing may be provided under the cover to provide the space in which the vacuum is formed.

It would be desirable to incorporate in such a bandage a system configured to irrigate the wound surface and to withdraw the irrigation fluids without removal of the bandage. Accordingly, a wound care bandage is provided for use with a vacuum source, the bandage comprising a wound dressing member to be placed in contact with the wound surface. The vacuum source may be any source of vacuum including a vacuum pump and collection canister arrangement to which the bandage is coupled by a tube set. The dressing member either has an access port coupled to it or it is associated with an access port, the port being connected to the vacuum source. The dressing member, which illustratively is a relatively thin and flexible member, has a wound contacting surface and an opposite surface, and a plurality of channels or space providing passageways coupled to the access port to provide communication with areas of the wound surface. The wound contacting surface of the member illustratively includes spacers contacting the wound to define a suction space between the member and the wound surface. The member includes suction holes which communicate with the suction space formed by the spacers. The bandage includes passageways between the port and the suction holes. In some embodiments of the invention, the passageways are provided by a plurality of channels formed in the opposite surface and a cover positioned over the channels.

In some embodiments, the spacers and suction space are defined by a plurality of channels formed in the wound contacting surface. Each of the channels formed in the wound contacting surface opens toward the wound surface and includes side edges contacting the wound.

In some embodiments of the invention, the dressing member has such a plurality of channels formed in patterns on both of the wound contacting surface and the opposite surface and the plurality of holes provide communication between the channels on both surfaces. In some embodiments, the channel patterns on the both surfaces are congruent or superimposed with both patterns radiating outwardly from the port and with the holes spaced radially along the channels.

In some embodiments, the dressing member is made from a material which is to be trimmed conformingly to fit the wound. In some embodiments, the dressing member is relatively transparent such that the condition of the wound surface can be observed through the wound member.

There is provided, therefore, a dressing for a wound, the dressing comprising a relatively thin flexible member which can be trimmed conformingly to fit the wound surface. A suction and irrigation port is associated with the dressing member, and a plurality of channels or passageways is formed in the member leading away from the port to provide communication between the port and areas of the wound surface. The dressing member is provided with a plurality of through holes in communication with the channels. A packing may be placed over the flexible member and a sealing film may be placed over the packing to seal around the perimeter of the wound to provide an enclosed space above the member in which a vacuum is formed by suction on the port. Irrigation fluid may be introduced to the port to impinge upon the wound surface and this fluid and wound exudate is removed from the space between the wound and the bandage member by suction applied to the port. It will be appreciated that the vacuum therapy and the irrigation therapy may take place without removal of the bandage. The illustrative member with the downwardly opening channels or spacers on the wound contacting surfaces provides a suction space which will uniformly apply the vacuum and the irrigation to the surface of the wound bed.

The covered channels on the opposite surface and the holes through the member further contribute to the ability to uniformly apply the vacuum therapy and irrigation fluid to the wound surface. A relatively large portion of the wound surface will be exposed to the vacuum therapy and irrigation using the illustrative bandage member. A large number of redundant passageways are provided for communicating from the access port directly to the wound surface. While some of the passageways may become blocked by exudate particles from the wound surface, other passageways will remain open for suction and irrigation.

The illustrative bandage, therefore, provides a relatively thin, flexible, comfortable bandage member which can be trimmed conformingly to fit into a wound bed and apply vacuum therapy and irrigation uniformly to the wound surface. The illustrative covered channel passageways on the opposite (upper or outer) surface provide a multitude of clearly defined passageways leading from the access port to the through holes leading directly into the suction space under the member.

Features of the invention will become apparent to those skilled in the art upon consideration of the following detailed description of preferred embodiments exemplifying the best mode of carrying out the invention as presently perceived.

BRIEF DESCRIPTION OF THE DRAWINGS

The detailed description particularly refers to the accompanying figures in which:

FIG. 7 is a sectional view of the bandage within the wound of the patient showing the wound surface, the wound contacting surface of the member adjacent the wound surface, the cover adjacent the opposite surface of the member, the tubing coupled to the port of the member, packing, and the outer film coupled to the patient's healthy skin to seal the environment;

FIG. 8 is another embodiment showing an alternate wound contacting surface of the member including spacers for contacting the wound surface to form an open space between the member and the wound surface;

FIG. 9 is a sectional view taken along line 9-9 of FIG. 8 showing one spacer and a through hole of the alternate member;

FIG. 10 is another embodiment showing an another wound contacting surface of the member including spacers or oblong ridges provided to form an open space between the member and the wound surface when the member is placed in the wound;

FIG. 11 is a sectional view taken along line 11-11 of FIG. 10 showing one oblong ridge and through hole of the alternate member;

FIG. 12 is another embodiment showing a wound care bandage having two ports;

FIG. 13 is another embodiment showing an alternate opposite surface of the member having ridges radially spaced around the port to provide a means of flow for exudate being vacuumed from the wound and/or for liquid being dispensed to the wound through the port;

FIG. 14 is a sectional view taken along line 14-14 of FIG. 13;

FIG. 15 is yet another embodiment showing a bandage having a plurality of ports each coupled to a vacuum/irrigation tube to provide an evenly distributed suction force across the member.

DETAILED DESCRIPTION OF THE DRAWINGS

Figure 1:
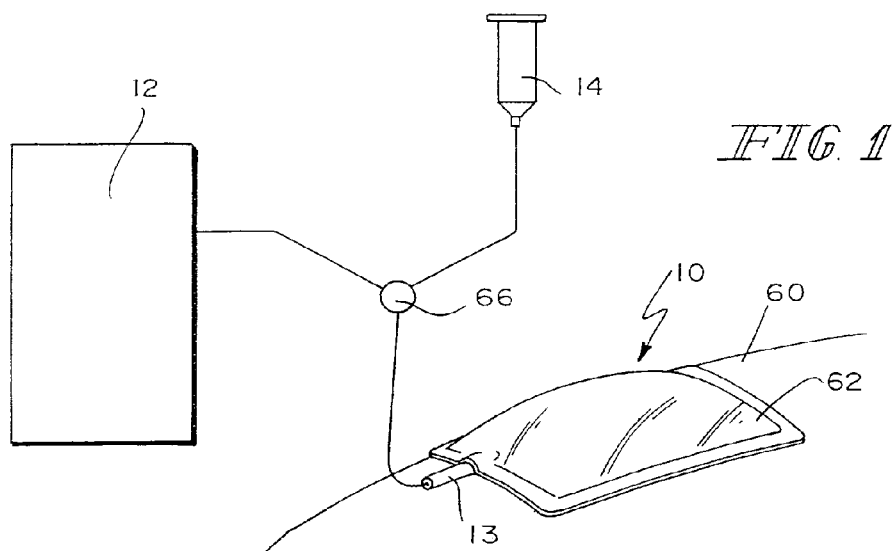
FIG. 1 is a part perspective part diagrammatic view of the wound care bandage showing the wound care bandage located on the leg of a patient and coupled to both a vacuum and an irrigation source through the use of a switch valve.

A wound care bandage 10 is provided for use with a vacuum and irrigation source 12, 14, respectively, as shown in FIG. 1. An illustrative vacuum and irrigation source 12, 14 is disclosed in application Ser. No. 09/725,666 filed simultaneous with this application and assigned to the same assignee. This application is specifically incorporated herein by reference.

Bandage 10 promotes the healing of a large wound 16 (shown in FIGS. 3 and 7) by providing vacuum therapy to the wound 16 to promote blood flow and remove exudate from a wound surface 18 of the wound 16 and by providing for irrigation of the wound 16 with fluids such as saline, for example. Reference is also made to with this U.S. patent application Ser. No. 09/369,113 (now U.S. Pat. No. 6,458,109) filed Aug. 5, 1999 and titled "Wound Treatment Apparatus". This pending application which is owned by the assignee of this present application is specifically incorporated herein by reference.

Figure 2:
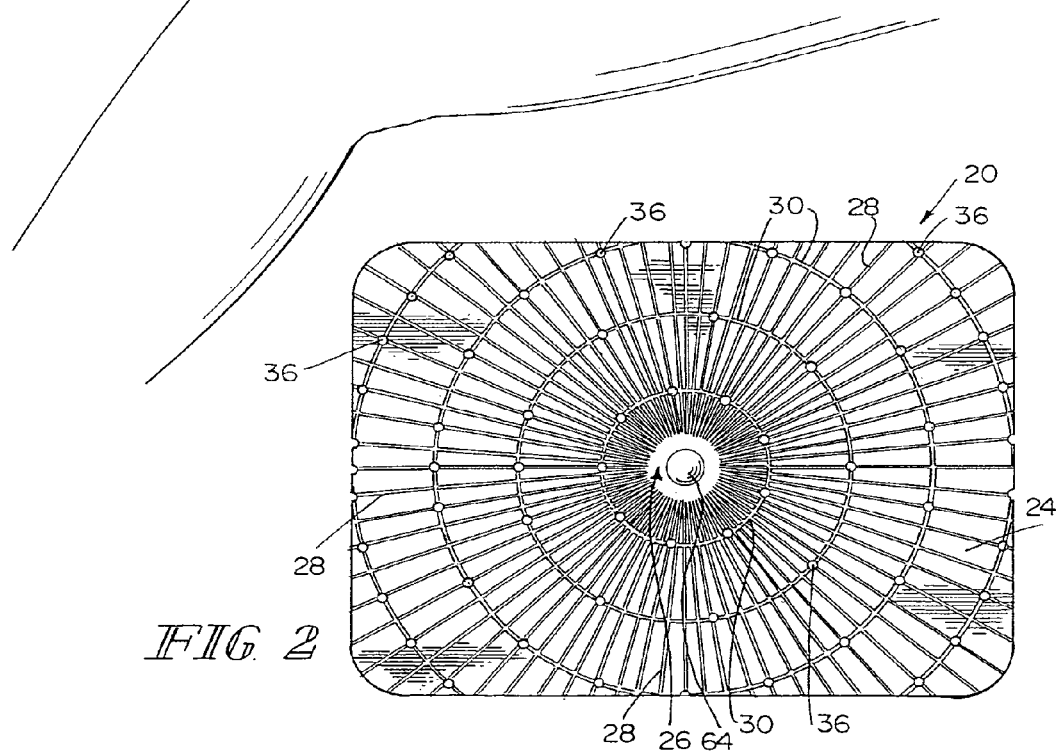
FIG. 2 is a top view of a member of the wound care bandage showing the member including a vacuum/irrigation port, a plurality of channels radiating outwardly from the port, and through holes which extend through the member.
Figure 3:
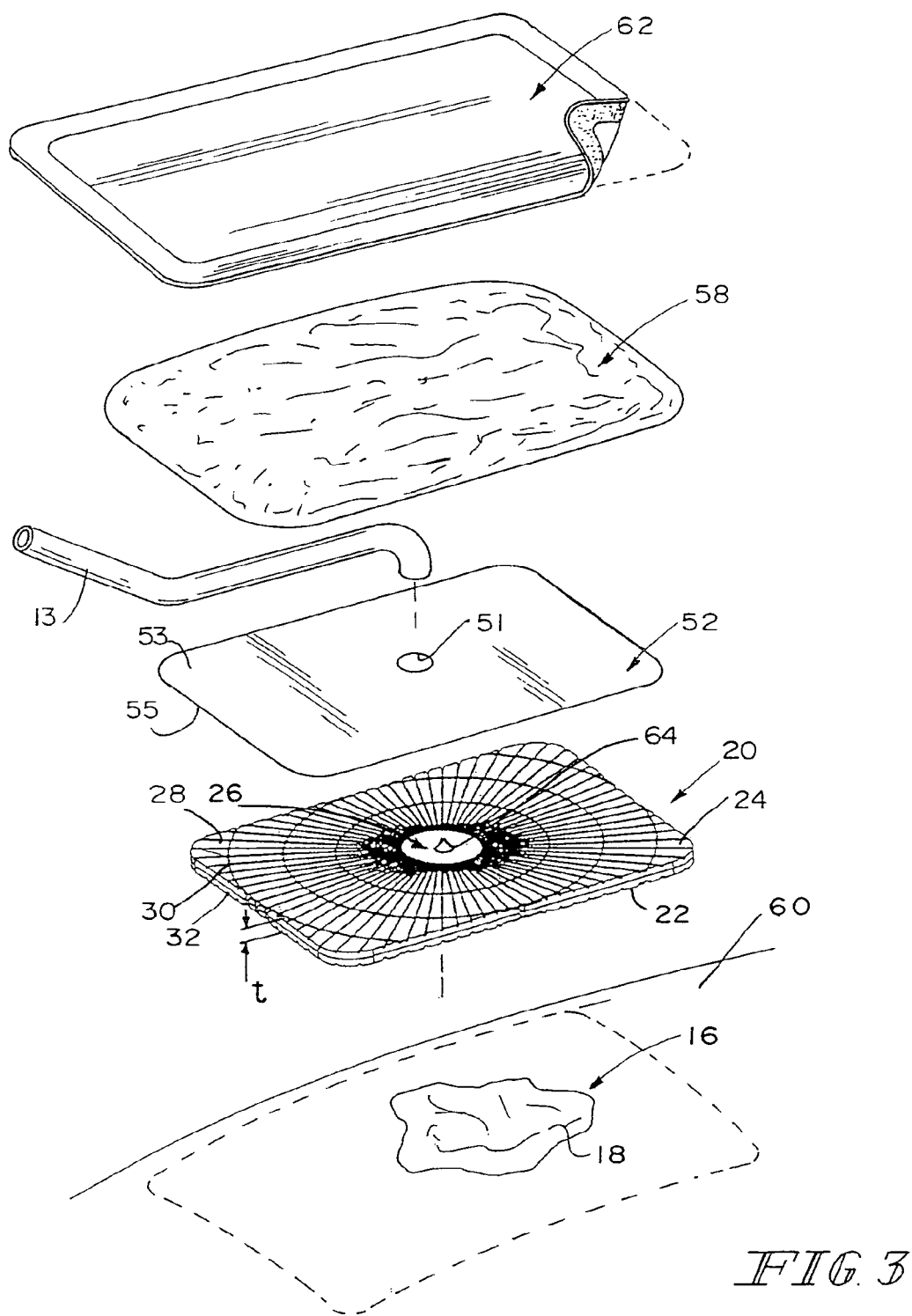
FIG. 3 is an exploded view of one embodiment of the wound care bandage showing the member having a wound contacting surface and an opposite surface, a cover adjacent the opposite surface, tubing which connects to the port of the member at one end and to the vacuum and irrigation sources at another end, packing to be placed on top of the tubing and member, and a sealing film which closes and seals the bandage to allow a vacuum environment to be created.

As shown in FIG. 3, wound care bandage 10 comprises a thin, flexible wound dressing member 20, shown in FIG. 2. Member 20 is made of a medical grade silicone or other type of elastomer which is pliable. Two companies, for example, which manufacture such medical grade silicone are GE Silicones and NuSil Technology. It is within the scope of this disclosure, however, to include a wound dressing member made of any type of thin, flexible material. Member 20 may be molded to include anti-microbial constituents. For example, it is within the scope of this disclosure to impregnate member 20 with silver ions which are known anti-microbials. The following PCT publications illustrate the use of antimicrobials in various products and are incorporated herein by reference: "Antimicrobial Plastic Closures for Drinking Containers", WO 00/26100; "Antimicrobial Contact Lens Case", WO 00/038552; "Antimicrobial Fabric and Medical Graft of the Fabric", WO 00/32247; "Antimicrobial Suturing Ring for Heart Valve", WO 00/30567.

Figure 4:
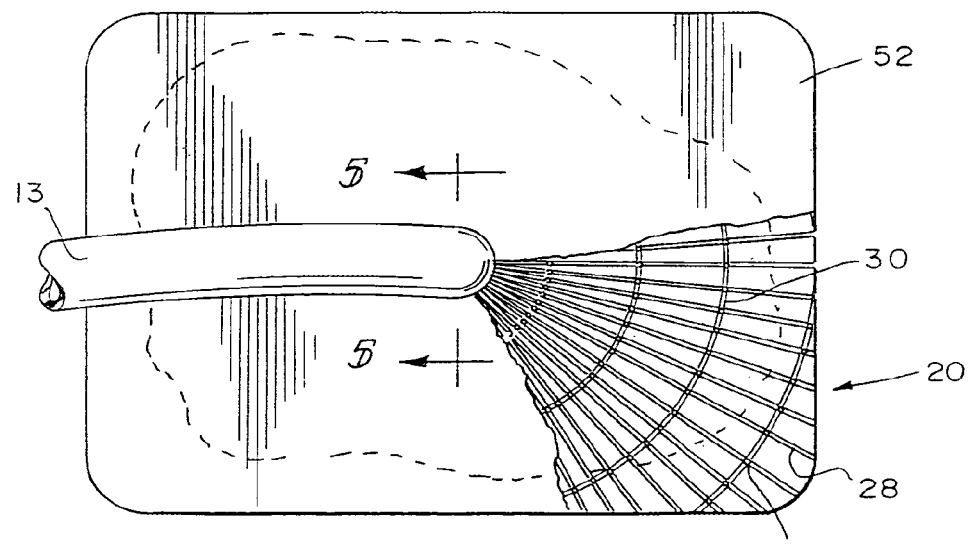
FIG. 4 is a top view of a portion of the bandage showing the cover with portions broken away and showing the member and the channels of the member enclosed by the cover in order to form passageways extending away from the port.
Figure 6:
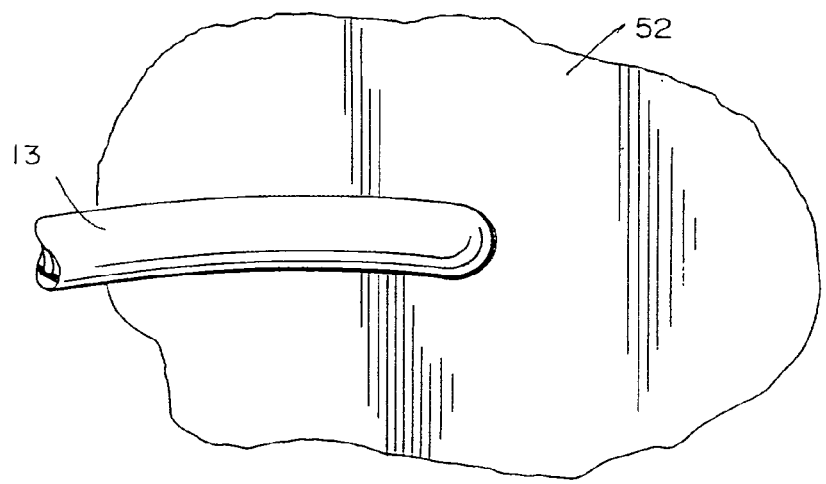
FIG. 6 is a top view of the portion of the member and cover shown in FIGS. 4 and 5 after having been trimmed to fit the particular wound of the patient.

As shown in FIG. 2, wound dressing member 20 is illustratively rectangular in shape. However, it is within the scope of the this disclosure for member 20 to be any suitable shape. Further, member 20 may be cut to fit any size wound 16, as shown in FIGS. 4 and 6. Member 20 is illustratively molded with a thickness of 0.080 inches. Illustratively, member 20 is made from a silicone of a Durometer 50A which is flexible with a thickness of 0.080 inches. It will be appreciated that the channel or passageways formed in the member will further contribute to its flexibility.

Figure 5:
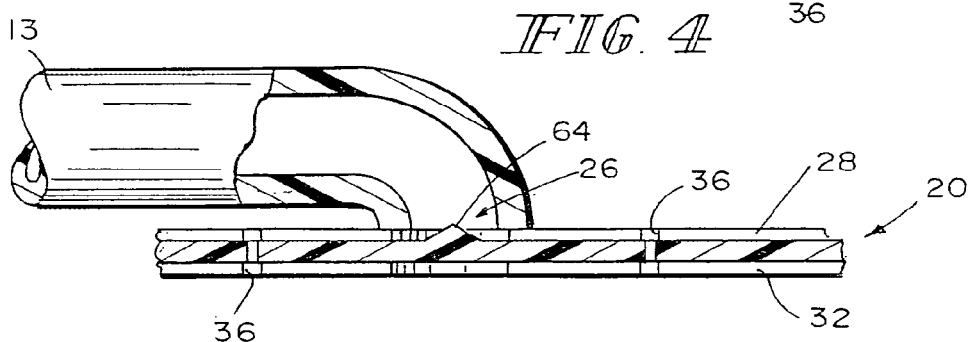
FIG. 5 is a sectional view taken along line 5-5 of FIG. 4 showing the tube which may be sealed to the port, showing a shallow cone of the port, and also showing the channels of the opposite surface and channels of the wound contacting surface and the holes which communicate between the channels.
Figure 16:
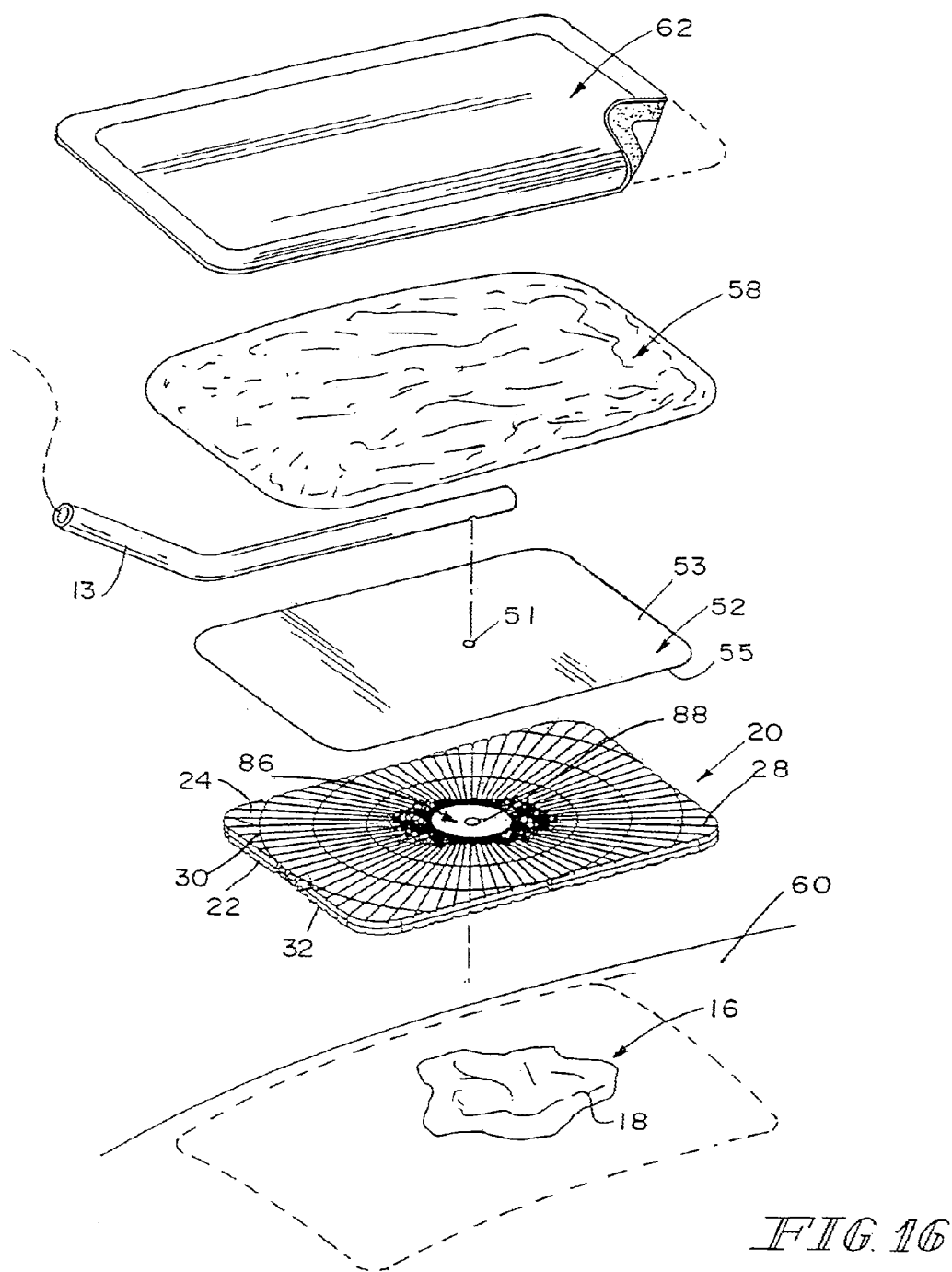
FIG. 16 is another embodiment showing a member of the bandage having a central aperture at the port of the member and channels extending radially outwardly from the central aperture.

Member 20 includes a wound contacting surface 22 and an opposite surface 24. Wound contacting surface 22 or portions thereof contact the wound surface 18 as shown in FIG. 7. Looking to FIG. 2, it can be seen that opposite surface 24 includes a central vacuum/irrigation port 26 and plurality of channels 28 extending radially away from port 26. Illustratively, each channel 28 is 0.030 inches wide and 0.030 inches deep. It is within the scope of the disclosure, however, to include channels 28 of the opposite surface 24 having other width and depth. Port 26, as shown in FIG. 5, includes a shallow cone 64 in order to induce fluids dispensed through a vacuum/irrigation tube 13 from the vacuum and irrigation sources 12, 14 to flow evenly into channels 28. In an alternate embodiment shown in FIG. 16, an alternate port 86 includes an aperture 88 formed through member 20. In the FIG. 16 embodiment, the port communications directly with the suction/irrigation space between the member 20 and the surface of the wound.

Vacuum/irrigation tube 13 is provided coupled to the port. The tube 13 may be molded as part of the member 20 or attached to the member by welding, adhesion or other known techniques. The tube is preferably made of silicone, however, it is within the scope of this disclosure to include a vacuum/irrigation tube made of other medically suited materials. Opposite surface 24 further includes channels 30 which are concentric with port 26, as shown in FIG. 2.

Wound contacting surface 22 includes a plurality of channels 32 which radiate outwardly from the center of member 20 similar to channels 28 of opposite surface 24. Similarly, wound contacting surface 22 also includes a plurality of channels 34 concentric with the center of member 20. Each channel 32, 34 of wound contacting surface 22 opens toward the wound surface 18 and includes outer edges 42 which contact the wound surface 18 or which act as spacers to provide space between the member 20 and the wound surface. Illustratively, the channels 32, 34 of wound contacting surface 22 have the same dimensions as the channels 28, 30 of opposite surface 24. In other words, illustratively channels 32, 34 of wound contacting surface 22 are 0.030 inches deep and 0.030 inches wide. However, it is within the scope of this disclosure to include channels 32, 34 of surface 22 to have other width and depth.

Through holes 36 are provided in member 20 for communication between the channels 28, 30 of the opposite surface 24 with the channels 32, 34 of the wound contacting surface 22. As shown in FIG. 2, holes 36 are illustratively positioned to lie within concentric channels 30, 34 of each respective surface 22, 24 of member 20. Holes 36 are illustratively 0.020 inches in diameter and are illustratively spaced approximately 0.500 inches apart along channels 28, 30 of each respective surface 22, 24. It is, however, within the scope of the disclosure to include holes having other suitable size diameter and other spacing.

Channels 32, 34 of wound contacting surface 22 provide open spaces 40 between the wound surface 18 and member 20, as shown in FIG. 7. Open spaces 40 are defined by each channel 32, 34 of wound contacting surface 22, each outer edge 42 of channels 32, 34, and wound surface 18. Each through hole 36 of member 20 opens into the open spaces 40 formed by channels 32, 34. Open spaces 40 allow vacuum source 12 to establish a generally uniformly distributed vacuum therapy to draw exudate from the wound 16 into the channels 32, 34 of wound contacting surface 22.

It is within the scope of this disclosure to provide spacers 46, for example, shown in FIGS. 8 and 9. Spacers 46 protrude outwardly from wound contacting surface 22 to contact wound surface 18. Open spaces 40 are provided between spacers 46. As shown in FIG. 9, each spacer 46 has an illustrative depth of approximately 0.030 inches. However it is within the scope of this disclosure to include spacers having other suitable dimensions which provide open spaces 40. As with member 20 including channels 32, 34 on wound contacting surface 22, holes 36 of member 20 including spacers 46 are positioned to open into the open spaces 40.

Further, it is within the scope of this disclosure to include member 20 having other types of spacers on wound contacting surface 22 which creates open spaces 40 when wound contacting surface 22 is adjacent the wound surface 18. In another embodiment, as shown in FIGS. 10 and 11, oblong ridges 50 are provided on wound contacting surface 22. Ridges 50 are similar in shape and function to spacers 46. Ridges 50 protrude away from member 20 and contact wound surface 18 when member 20 is place on wound surface 18 to provide open spaces 40 between wound surface 18 and member 20 to establish a generally uniform vacuum across the wound surface 18. As shown in FIG. 11, each ridge 50 illustratively has a preferred depth of 0.030 inches, however, a ridge having other suitable dimensions is within the scope of this disclosure. As illustrated by channels 32, 34 of wound contacting surface 22, spacers 46, or ridges 50, it is within this disclosure to include other structures which acts as spacers to create open spaces 40 between the wound surface 18 and member 20 when member 20 is placed on the wound surface 18 to distribute suction and irrigation generally uniformly throughout the wound 16.

Bandage 10 further comprises a cover 52 for opposite surface 24 of member 20. Cover 52 is provided to cover channels 28, 30 of opposite surface 24. Cover 52 and channels 28 of opposite surface 24 cooperate to form passageways 56, as shown in FIG. 7, extending away from port 26. Passageways 56 are also formed by the cooperation of concentric channels 30 of opposite surface 24 and cover 52. Cover 52 is adhered to member 20 through the use of an adhesive or other suitable means. It will be appreciated that the covered channels 28, 30 provide an ideal way to fabricate a multitude of passageways 56 communicating with the wound surface. In an alternate embodiment, passageways 56 are formed by cooperation of ridges 54 on opposite surface 24 of member 20, rather than channels 30, and cover 52, as shown in FIGS. 13 and 14, for example. It is within the scope of this disclosure to include a bandage 10 forming other passageways 56 extending away from port 26. Holes 36 of member 20 having ridges 54 are located within passageways 56 of bandage 10 similar to holes 36 of member 20 having radial channels 28 and concentric channels 30.

It will be appreciated that the illustrative cover 52 may be provided with scale marking for gauging the wound size or healing progress. Circular markings may be added at 0.5 cm or 1.0 cm intervals to provide convenient measuring of the wound and healing progress.

As shown in FIGS. 3 and 7, bandage 10 further includes gauze or other suitable packing 58 which lies on top of cover 52 and is provided to fill the wound 16 up to the surface of the patient's healthy skin 60. A sealing film 62 of bandage 10 is placed over packing 58. Film 62 is provided to cover the entire wound 16 and to extend across and attach to the patient's healthy skin 60, as shown in FIGS. 1 and 7. Preferably, film 62 is an occlusive or semi-occlusive material which allows water vapor to permeate through. Because of this characteristic, the film 62 is referred to as Moisture Vapor Transmission Rate film or MVTR film. The products Tegaderm™, made by 3M, and OpSite™ by Smith and Nephew can be used for film 62, for example. The product OpSite™ is a semi-permeable film. Film 62 is approximately 0.003 inches thick, however, it is within the scope of this disclosure to include any occlusive or semi-occlusive film 62 having other thickness.

As shown in FIG. 7, vacuum/irrigation tube 13 or an extension added to the tube 13 extends over the edge of member 20 and cover 52 and out from under the edge of the sealing film 62. In use, irrigation source 14 delivers liquid through tube 13 to port 26 and onto the top of a shallow cone 64 of member 20 which extends upwardly as shown in FIGS. 5 and 7. Cone 64 acts to spread the liquid out through the passageways 56 formed by the cooperation of channels 28, 30 (or ridges 54) and cover 52. The fluid moves radially out through passageways 56 to holes 36. The fluid then moved down through holes 36 to open spaces 40 to impinge on wound surface 18.

A switch valve 66 is illustratively provided, as shown in FIG. 1, to allow a user to switch between the use of the vacuum source 12 and the irrigation source 14. It will be appreciated that mechanism other than the switch valve 66 may be used selectively to couple the vacuum source or the irrigation source to the bandage. Simple tube clamps, for example, may be used selectively to open and close the tube set provided with the bandage 10. When valve 66 is switched to operate the vacuum source 12, the vacuum suction draws exudate into the open spaces 40 and up through the holes 36. The exudate is then drawn radially inwardly through passageways 56 toward port 26 and finally through tube 13. Although illustrative bandage 10 includes one central port 26, it is within the scope of this disclosure to include multiple ports 70, as shown in FIGS. 12 and 15, for example. Bandage 10 may make use of two ports 70 located at opposite ends of member 20, as shown in FIG. 12. Alternately, as shown in FIG. 15, bandage 10 may make use of a plurality of ports 70 spaced throughout member 20. It is contemplated that, in some embodiments having two ports, one port may be used for suction or vacuum therapy and the other port may be used for irrigation therapy.

It is contemplated that irrigation source 14 may be operated to provide irrigation fluid at various selected pressures. It is also contemplated that the bandage 10 and dressing member 20 may be provided in various sizes and shapes. The dressing member 20 may be reused with a single patient. It is also contemplated that the dressing 10 may be used with manual irrigation (nurse uses the syringe manually) as well as the powered syringe 14.

Although this invention has been described in detail with reference to certain embodiments, variations and modifications exist within the scope and spirit of the invention as described and defined in the following claims.

What is claimed is:

1. A wound treatment apparatus comprising:
   a vacuum source;
   a bandage configured to be coupled to the vacuum source, the bandage comprising a wound dressing member configured to be placed in contact with a wound surface, the wound dressing member having:
   a plurality of spacers configured to contact the wound surface to define suction space between the wound dressing member and wound surface;
   a suction port associated with the wound dressing member and configured to be connected to the vacuum source;
   a plurality of suction holes configured to communicate with the suction space; and
   a plurality of passageways between the suction port and the suction holes.

2. The apparatus of claim 1, where the wound dressing member comprises a relatively thin, flexible member configured to be trimmed conformingly to fit the wound surface, the member having a wound contacting surface including the spacers and an opposite surface.

3. The apparatus of claim 2, where the passageways of the wound dressing member are provided by channels formed in the opposite surface extending away from the suction port and a cover over the channels.

4. The apparatus of claim 3, where the spacers and suction space are defined by a plurality of channels formed in the wound contacting surface, and where the channels of the wound contacting surface open toward the wound surface and include side edges contacting the wound.

5. The apparatus of claim 4, where the suction holes of the wound dressing member extend between the channels on the wound contacting surface and the channels on the opposite surface.

6. The apparatus of claim 1, further comprising:
   a fluid source configured to be coupled to the bandage such that the irrigation fluid can be distributed to the wound surface through the suction holes of the wound dressing member and the suction space.

7. The apparatus of claim 1, where the bandage further comprises a cover configured to cover the member and to be coupled to healthy skin surrounding the wound to define a space above the wound surface where a vacuum can be formed if the port is connected to the vacuum source.

8. A wound treatment apparatus comprising:
   a vacuum source; and
   a wound care bandage configured to be coupled to the vacuum source, and comprising a thin, flexible member configured to be trimmed to fit a wound and placed in contact with the wound surface such that a space is provided between the member and the wound surface, the member having a plurality of holes configured to communicate with the space, a port associated with the member, and passageways extending from the port to the holes.

9. The apparatus of claim 8, where the member includes a wound contacting surface and an opposite surface, the bandage further includes a cover adjacent the opposite surface, and the passageways are defined by a plurality of channels formed in the opposite surface and the cover.

10. The apparatus of claim 9, where the opposite surface of the member further includes a plurality of channels concentric with the port and wherein the holes of the member are aligned with the concentric channels.

11. The apparatus of claim 8, where the member includes a wound contacting surface and a plurality of spacers adapted to contact the wound surface to provide the space between the member and the wound.

12. The apparatus of claim 11, where the spacers of the member are defined by a plurality of channels in the wound contacting surface, each including outer edges configured to contact the wound surface.

13. The apparatus of claim 8, where the bandage further comprises a cover configured to cover the member and to be coupled to healthy skin surrounding the wound to define a space above the wound surface where a vacuum can be formed if the port is connected to the vacuum source.

14. A wound treatment apparatus comprising:
a vacuum source; and
a wound care bandage configured to be coupled to the vacuum source, and comprising: a wound dressing member configured to be placed in direct contact with a wound surface, the wound dressing member having at least one access port configured to be connected to the vacuum source, a wound contacting surface, an opposite surface, and a plurality of channels on the wound contacting surface configured such that if the wound contacting surface is placed in contact with the wound surface the plurality of channels on the wound contacting surface open toward the wound surface to provide communication with areas of the wound surface.

15. The apparatus of claim 14, where the opposite surface of the wound dressing member includes a plurality of channels extending away from the access port.

16. The apparatus of claim 15, where the wound contacting surface and the opposite surface of the wound dressing member each include a plurality of additional channels concentric with the access port.

17. The apparatus of claim 14, where the wound dressing member comprise flexible material configured to conformingly rest against the wound surface.

18. The apparatus of claim 17, where the wound dressing member comprises a material configured to be trimmed conformingly to fit the wound.

19. The apparatus of claim 17, where the wound dressing member includes a plurality of holes opening from the opposite surface to the wound contacting surface.

20. The apparatus of claim 19, where the plurality of holes connect the channels of the wound contacting surface with the channels of the opposite surface.

21. The apparatus of claim 14, where the opposite surface of the wound dressing member includes a plurality of channels, and the wound dressing member further includes a plurality of holes providing communication between the channels on the wound contacting surface and the channels on the opposite surface.

22. The apparatus of claim 21, where channels on the surfaces of the wound dressing member extend radially outward from the access port and the holes are spaced radially along the channels.

23. The apparatus of claim 21, where the bandage comprises a cover over the opposite surface to cover the channels on the opposite surface.

24. The apparatus of claim 14, where the wound dressing member comprises a relatively thin, flexible, sheet-like member configured to conformingly rest against a wound surface, and the wound dressing member includes a plurality of holes opening through the wound contacting surface.

* * * * *